United States Patent
March et al.

(10) Patent No.: US 10,683,482 B2
(45) Date of Patent: Jun. 16, 2020

(54) STEM CELL CONDITIONED MEDIA AND METHODS OF USING THE SAME

(71) Applicant: NeuroFx, Inc., Indianapolis, IN (US)

(72) Inventors: Keith Leonard March, Carmel, IN (US); Brian H. Johnstone, Indianapolis, IN (US); Yansheng Du, Westfield, IN (US)

(73) Assignee: NeuroFx, Inc., Indianapolis, IN (US)

( * ) Notice: Subject to any disclaimer, the term of this patent is extended or adjusted under 35 U.S.C. 154(b) by 0 days.

(21) Appl. No.: 15/860,187

(22) Filed: Jan. 2, 2018

(65) Prior Publication Data

US 2018/0187159 A1 Jul. 5, 2018

Related U.S. Application Data

(63) Continuation of application No. 14/949,380, filed on Nov. 23, 2015, now Pat. No. 9,856,455, which is a continuation of application No. 13/477,237, filed on May 22, 2012, now Pat. No. 9,192,632, which is a continuation of application No. 13/236,566, filed on Sep. 19, 2011, now abandoned, and a continuation of application No. 13/236,390, filed on Sep. 19, 2011, now abandoned, said application No. 13/236,566 is a continuation of application No. 11/844,941, filed on Aug. 24, 2007, now Pat. No. 8,021,882, said application No. 13/236,390 is a continuation of application No. 11/844,941, filed on Aug. 24, 2007, now Pat. No. 8,021,882.

(60) Provisional application No. 60/823,460, filed on Aug. 24, 2006.

(51) Int. Cl.
| | |
|---|---|
| C12N 5/00 | (2006.01) |
| C12N 5/02 | (2006.01) |
| C12N 5/071 | (2010.01) |
| A61K 35/28 | (2015.01) |
| C12N 5/0775 | (2010.01) |
| C12N 5/0793 | (2010.01) |
| A61K 35/35 | (2015.01) |
| C12N 5/07 | (2010.01) |

(52) U.S. Cl.
CPC ............ *C12N 5/0667* (2013.01); *A61K 35/28* (2013.01); *A61K 35/35* (2013.01); *C12N 5/0619* (2013.01); *C12N 5/06* (2013.01); *C12N 5/0663* (2013.01); *C12N 5/0668* (2013.01); *C12N 2502/00* (2013.01); *C12N 2502/1305* (2013.01); *C12N 2502/1352* (2013.01); *C12N 2502/1358* (2013.01); *C12N 2502/1382* (2013.01)

(58) Field of Classification Search
CPC ............... C12N 5/0663; C12N 5/0668; C12N 2502/1352; C12N 2502/1358; C12N 2502/1382; A61K 35/28

USPC .......................... 435/372, 404, 405; 424/574
See application file for complete search history.

(56) References Cited

U.S. PATENT DOCUMENTS

| | | | |
|---|---|---|---|
| 7,470,537 B2 | 12/2008 | Hedrick et al. | |
| 7,807,464 B2 | 10/2010 | Zhang et al. | |
| 2004/0005661 A1 | 1/2004 | Minger et al. | |
| 2005/0244964 A1 | 11/2005 | Davidson | |
| 2005/0250202 A1 | 11/2005 | March et al. | |
| 2006/0045872 A1 | 3/2006 | Miguel et al. | |
| 2006/0057722 A1 | 3/2006 | Kornowski et al. | |
| 2006/0165667 A1 | 7/2006 | Laughlin et al. | |
| 2006/0182724 A1 | 8/2006 | Riordan | |
| 2012/0294949 A1 | 11/2012 | Johnstone et al. | |
| 2013/0195991 A1 | 8/2013 | Ueda et al. | |

OTHER PUBLICATIONS

Horn et al., 2009, Neuroscience Research, 63: 35-41.*
Wei et al., 2009, Stem Cells, 27: 478-488.*
Bryan et al., 2013, http://www.elsevierblogs.com/currentcomments/?p=962, Implications of protein fold switching, p. 1-4.*
Kim et al., 2014, IOVS, vol. 55, No. 8, p. 5099-5108.*
Kolf et al., 2007, Arthritis Research & Therapy, vol. 9, p. 204, 10 pages.*
Alenzi et al., 2011, African Journal of Biotechnology, vol. 10(86), pp. 19929-19940.*
Abeyta, M., et al. "Unique gene expression signatures of independently-derived human . . . ". Human Molecular Genetics, 2004, pp. 601-608. vol. 13, Oxford University Press.
Allegrucci, C., et al. "Differences between human embryonic . . . ", Human Reproduction Updated, 2007, pp. 103-120, vol. 13, No. 2 (advance access pub., pp. 1-18), Aug. 26, 2006.
Chattopadhyay, et al. "Effect of single amino acid mutations in the conserved GDNQ motif . . . ", Virus Research 99, 2004, pp. 139-145, Elsevier.
Rao, et al. "Conserved and divergent paths that regulate self-renesal in mouse . . . ", Developmental Biology 275, 2004, pp. 269-286, Elsevier.
Rehman, et al. "Secretion of Aniogenic and Antiapoptotic Factors by Human Adipose Stromal Cells", Circulation 2004, vol. 109, pp. 1292-1298.
Sato, et al. "Molecular signature of human embryonic stem cells and its comparison with the mouse", Developmental Biology 260, 2003, pp. 404-413, Elsevier.

(Continued)

*Primary Examiner* — Shin Lin Chen
(74) *Attorney, Agent, or Firm* — Reichel Stohry Dean LLP; Mark C. Reichel; Natalie J. Dean

(57) ABSTRACT

Methods of producing stem cell conditioned media to treat mammalian injuries or insults. In at least one embodiment of a method of producing a stem cell conditioned media of the present disclosure, the method comprises the steps of culturing at least one stem cell in a first cell culture medium, replacing some or all of the first cell culture medium with a second cell culture medium and further culturing the at least one stem cell in the second cell culture medium, and collecting a quantity of the second cell culture medium after a culture duration, wherein the quantity of the second cell culture medium contains a cell culture byproduct effective to treat a mammalian insult or injury.

14 Claims, 20 Drawing Sheets

(56) References Cited

OTHER PUBLICATIONS

Skolnick, et al. "From genes to protein structure and function: novel applications . . . ", Tibtech, Jan. 2000. vol. 18, pp. 34-39, Elsevier.
Smallwood, et al. "Different Substitutions at Conserved Amino Acids in Domains II . . . ", Virology 304, 2002, pp. 135-145.
Tomasinsig, et al. "The Cathelicidins—Structure, Function and Evolution", Current Protein and Peptide Science, 2005, vol. 6, pp. 23-24.
Torchilin et al. "Peptide and protein drug delivery to and into tumors . . . ", Drug Discovery Today, vol. 8, No. 6, Mar. 2003, pp. 259-266.
Hamman, et al. "Oral Delivery of Peptide Drugs", Drug Delivery Biodrugs, 2005 vol. 19, No. 3, pp. 165-177.
Yanez, et al. "In vitro and in vivo immunomodulatory effects of mesenchymal . . . ", Blood, Nov. 16, 2005, vol. 106, No. 11, Part 1, pp. 866A, Amer Soc Hematol, Atlanta, GA, USA.
Bourin, et al. "Stromal cells from the adipose tisue-derived stromal . . . ", a joint statement of IFATS and ISCT, Cytotherapy, 2013, vol. 15, pp. 641-648.
Gimble, et al. "Human adipose-derived cells: an update on the transition to clinical translation", Regen. Med., Mar. 2012, vol. 7, No. 2, pp. 225-235.
Grumbles, et al., "Neurotrophic Factors Improve Mononeuron Survival and function of Muscle Reinnervated . . . ", J Neuropathol Exp Neurol, Jul. 2009, vol. 68, No. 7, pp. 736-746.
Johnson, et al., "Adipose-Derived Stem Cell Collection and Characterization in Bottlenose . . . ", Stem Cell and Development, 2012 vol. 21, No. 16 pp. 2949-2957.
Mitragotri, et al., "Overcoming the challenges in administering biopharmaceuticals: formulation . . . ", Nature Reviews, Drug Discovery, Sep. 2014, vol. 13, pp. 655-672.
Mohammadi-Sangchesmeh, et al., "Isolation, characterization, and mesodermic . . . ", In Vitro Cell, Dev. Biol. Anim. Feb. 2013, vol. 49, No. 2, pp. 147-154.
Murphy, et al., "Mesenchymal stem cells: environmentally responsive . . . ", Experimental & Molecular Medicine, 2013, 45, e54, doi.1038/emm.2013.94.
Rehman, et al., "Peripheral blood "Endothelial Progenitor cells" Are Derived From . . . ", Circulation, 2003, vol. 107, pp. 1164-1169.
Alenzi, et al., "Stem cells: Biology and clinical potential", African Journal of Biotechnology, Dec. 30, 2011, vol. 10 (86), pp. 19929-19940, Academic Journals.
Bhang, et al., "Efficacious and Clinically Relevant Conditioned Medium of Human . . . ", vol. 22, No. 4, pp. 862-872, Apr. 2014, The American Society of Gene & Cell Therapy.
Hashemi, et al., "Comparative Immunomodulatory Properties of Adipose-Derived . . . ", Journal of Cellular Biochemistry, 2013, vol. 114, pp. 955-965.
Kolf, et al., "Biology of adult mesenchymal stem cells . . . ", Feb. 19, 2007, Arthritis Research & Therapy, vol. 9, No. 204, pp. 1-10.
Mischen, et al., "Metabolic and Functional Charaterization of Human Adipose-Derived . . . ", Sep. 2008, vol. 122, No. 3, Plastic and Reconstructive Surgery, pp. 725-738.
Pandey, Prativa, 2007, Abstracts, 59th Southeast Reginoal Meeting of American Chemical Society, Greenville, SC, USA, GEN-671: American Chemical Society, Washington DC.
Whitehurst, et al., "Single and multiple deetions in the transmembrane domain . . . ", Virology 347 (2006), pp. 199-2017, Elsevier.

* cited by examiner

The Morris Water Maze test using a visible platform was performed at 7 weeks after HI injury (**, P<0.01).

STEM CELL CONDITIONED MEDIA AND METHODS OF USING THE SAME

PRIORITY

The present application is related to, claims the priority benefit of, and is a U.S. continuation application of, U.S. Nonprovisional patent application Ser. No. 14/949,380, filed Nov. 23, 2015 and issued as U.S. Pat. No. 9,856,455 on Jan. 2, 2018, which is related to, claims the priority benefit of, and is a U.S. continuation application of, U.S. Nonprovisional patent application Ser. No. 13/477,237, filed May 22, 2012 and issued as U.S. Pat. No. 9,192,632 on Nov. 24, 2015, which is related to, claims the priority benefit of, and is a U.S. continuation application of, (i) U.S. Nonprovisional patent application Ser. No. 13/236,390, filed Sep. 19, 2011, now abandoned, and (ii) U.S. Nonprovisional patent application Ser. No. 13/236,566, also filed Sep. 19, 2011, now abandoned, both of which are related to, claim the priority benefit of, and are continuation applications of, U.S. Nonprovisional patent application Ser. No. 11/844,941, filed Aug. 24, 2007 and issued as U.S. Pat. No. 8,021,882 on Sep. 20, 2011, which is related to, and claims the priority benefit of, U.S. Provisional Patent Application Ser. No. 60/823,460, filed Aug. 24, 2006. The contents of each of these applications and patents are hereby incorporated by reference in their entirety into this disclosure.

BACKGROUND

Pluripotent cells, sometimes referred to as stem cells, are characterized by an ability to differentiate into a variety of different cells. Some pluripotent cells types, such as human embryonic stem cells, display an ability to differentiate into the broadest spectrum of cells; in fact, embryonic stem cells display an ability to differentiate into practically any type of cell that exists within the human tissues. However, as embryonic stem cells develop and differentiate into lines of partially and/or fully differentiated cells, those further differentiated cells lose some or all of their pluripotent ability because embryonic stem cells have the ability to "morph" into practically any cell type, the scientific community has explored the possibility of using these embryonic stem cells to replace those injured or dying cells in individuals suffering neurodegenerative disease such as Parkinson's disease.

However, embryonic stem cells have limitations in their ability to be used clinically, as they must be derived from another individual—an embryo. This not only raises a potential that the patient will reject the cells, but it also severely limits the ability for such cells to be used in the first place. Therefore, much effort has been made in finding pluripotent cells that are obtainable in large quantities, that can differentiate into a target cell, and that will not be rejected by the individual being treated thereby. One such pluripotent cell that has been used for autologous cell therapy to regenerate neural tissue is the pluripotent cells found in the "stromal" or "non-adipocyte" fraction of the adipose tissue. These pluripotent cells were previously considered to be pre-adipocytes, i.e. adipocyte progenitor cells (hereinafter "adipose stem cells" or "ASC"). Zuk, 2001. Data suggests that these adipose stem cells have a wide differentiation potential, as research by Zuk using subcutaneous human ASCs in vitro were able to be differentiated into adipocytes, chondrocytes and myocytes. Id. Further studies by Erickson et al., showed that human ASCs could differentiate in vivo into chondrocytes following transplantation into immune-deficient mice, and studies by Stafford showed that human ASCs were able to differentiate into neuronal cells. (Erickson, 2002); (Stafford, 2002). More recently, it was demonstrated that human ASCs were able to differentiate into neuronal cells, osteoblasts (Dragoo, 2003), cardiomyocyte (Rangappa, 2003; Planat-Benard, 2004), and endothelial cells (Planat-Benard, 2004). As such studies suggest that the delivery of certain pluripotent cells to neural tissue damaged by stroke or cardiovascular disease may cause regeneration of the damaged tissue through differentiation of the delivered pluripotent cells.

Therefore, treatments using autologous pluripotent cells, and ASCs in particular, have necessarily centered upon the harvest and concentration of the pluripotent cells from a remote area of the patient to be treated, followed by application of those concentrated pluripotent cells to an injured or targeted site so that the pluripotent cells can differentiate and take the place of the damaged cells at the target. See, e.g., U.S. Pat. No. 7,078,230 to Wilkison et al.; U.S. Patent App. Pub. No. U.S. 2005/0260174 to Fraser et al.

BRIEF SUMMARY

At least embodiment of the present disclosure provides harvesting adipose stem cells (ASC) recovered from adipose tissue to provide an autologous source of cells. These pluripotent cells, which reside in the "stromal" or "non-adipocyte" fraction of the adipose tissue, have the capacity to differentiate in culture into adipocytes, chondrocytes, osteoblasts, neuronal cells, and myotubes. ASCs can be obtained in large quantities, in the range of $10^8$ to $10^9$ cells, following routine liposuction of subcutaneous adipose tissue. The ready accessibility of these cells provides for a particularly feasible and attractive form of cells for harvest and presents the opportunity to retrieve a given patient's own cells as a source of pluripotent cells for harvesting.

Another embodiment of the present disclosure relates to the use of harvested ASCs or other stem cells to secrete bioactive levels of therapeutic proteins that can promote repair of injured and diseased neural tissues or prevent neural tissue death under circumstances that would ordinarily result in apoptosis. According to one aspect, still another embodiment relates to using media exposed to ASCs maintained and/or growing in cell culture to produce a composition that promote the growth, health, protection, and/or development of various types of human and animal cells, especially neural cells.

Yet another embodiment of the present disclosure relates to the use of at least one factor produced by ASCs to effect changes in other cells exposed to the factors. In one embodiment, at least one factor produced by an ASC is used to prevent the death of neuronal cells either in culture or in the central or peripheral nervous system of an adult or developing animal, including *Homo Sapiens*.

Still another embodiment of the present disclosure related to a method of treating diseases, disorders or injuries in neural tissue by exposing neuronal tissues and various cells therein to products produced by ASCs.

Still another embodiment of the present disclosure relates to using media exposed to ASCs to modulate physiological processes such as formation of new vessels or expansion of existing vessels within the central nervous system, peripheral nervous system, or spinal cord. At least one embodiment relates to a method of treating at least a portion of the central nervous system comprising the steps of administering at least a fractionated portion of the media exposed to ASC to at least one region of the Central Nervous System in either a human or animal patient.

At least one embodiment of the present disclosure relates to a method of using substances secreted by ASCs into the cell culture medium to modulate at least one of several in vitro neuronal injury pathways.

Still another embodiment of the present disclosure relates to recovery of at least one compound produced by ASCs in cell culture to a cell culture media in contact with ASCs to modulate the activity of neuronal cells.

Yet another embodiment of the present disclosure relates to using at least substance derived from ASC media cultured in vitro to treat cells in vivo at risk for ischemic-hypoxia-induced neuronal death.

Another embodiment of the present disclosure relates to the in vitro use at least one of substances derived from ASC cells cultured in vitro to affect the activity, viability and/or differentiation of neuronal cells either in vivo or in vitro.

Still another embodiment of the present disclosure is a method of treating hippocampal tissue that has been damaged by neonatal hypoxia-ischemia comprising the steps of providing at least substance or compound derived from media recovered from cultures of ASCs and administering at least one dosage of the at least one factor to hippocampal neuron tissue and/or cells.

In at least one embodiment of a method of producing a stem cell conditioned media of the present disclosure, the method comprises the steps of culturing at least one stem cell in a first cell culture medium, replacing some or all of the first cell culture medium with a second cell culture medium and further culturing the at least one stem cell in the second cell culture medium, and collecting a quantity of the second cell culture medium after a culture duration, wherein the quantity of the second cell culture medium contains a cell culture byproduct effective to treat a mammalian insult or injury. In another embodiment, the step of culturing comprises culturing the at least one stem cell in EGM2MV. In yet another embodiment, the step of replacing comprises replacing some or all of the first cell culture medium with the second cell culture medium selected from the group consisting of BME and EBM-2. In an additional embodiment, the step of replacing comprises replacing some or all of the first cell culture medium with a basal medium that is at least substantially growth factor-free. In yet an additional embodiment, the step of collecting comprises collecting the quantity of the second cell culture medium containing at least one factor selected from the group consisting of at least one angoigenic factor and at least one antiapoptotic factor.

In at least one embodiment of a method of producing a stem cell conditioned media of the present disclosure, the method further comprises the step of administering the cell culture byproduct to a patient having the mammalian insult or injury. In an additional embodiment, the step of administering comprises administering the cell culture byproduct to the patient having a mammalian neural insult or injury, wherein the cell culture byproduct comprises at least one factor capable of treating the mammalian neural insult or injury. In an additional embodiment, the step of culturing comprises culturing the at least one stem cell obtained from an individual selected from the group consisting of the patient and a mammal who is not the patient. In another embodiment, the method further comprises the step of concentrating the quantity of the second cell culture medium to a concentration selected from the group consisting of at least 50-fold, between 50-fold and 100-fold, at least 100-fold, between 100-fold and 250-fold, and at least 250-fold.

In at least one embodiment of a method of producing a stem cell conditioned media of the present disclosure, the method further comprises the step of fractionating the quantity of the second cell culture medium to remove substances less than a specified kDa range selected from the group consisting of less than about 5 kDa, less than about 10 kDa, less than about 20 kDa, less than about 30 kDa, less than about 40 kDa, less than about 50 kDa, and greater than about 50 kDa. In another embodiment, the step of culturing comprises culturing the at least one stem cell selected from the group consisting of a human adipose stem cell, a human mesenchymal stem cell, a human pluripotent stem cell from skeletal muscle, a human brain stem cell, a human common pluripotent stem cell, a human progenitor cell derived from a mesenchymal stem cell, a non-human adipose stem cell, a non-human mesenchymal stem cell, a non-human pluripotent stem cell from skeletal muscle, a non-human brain stem cell, a non-human common pluripotent stem cell, and a non-human progenitor cell derived from a mesenchymal stem cell. In yet another embodiment, the step of culturing comprises culturing the at least one stem cell in the first cell culture medium comprising a first amount of growth factor, and wherein the step of replacing comprising replacing some or all of the first cell culture medium with the second cell culture medium having a second amount of growth factor, and wherein the second amount is less than the first amount. In an additional embodiment, the step of culturing comprises culturing the at least one stem cell having a surface marker profile selected from the group consisting of lin-/CD45-/c-kit-/CD90+ and lin-/CD45-/c-kit-/CD90+/CD34. In yet an additional embodiment, the step of culturing comprises culturing the at least one stem cell to confluence.

In at least one embodiment of a method of producing a stem cell conditioned media of the present disclosure, the step of replacing comprises replacing some or all of the first cell culture medium with the second cell culture medium for conditioning in either normoxic or hypoxic conditions. In an additional embodiment, the method further comprises the step of processing the quantity of the second cell culture medium using a process selected from the group consisting of centrifugation, concentration, fractionation, lyophilization, and freeze-drying, to create a processed product.

In at least one embodiment of a method of producing a stem cell conditioned media of the present disclosure, the method comprises the steps of culturing at least one stem cell in a first cell culture medium comprising EGM2MV and having a first amount of growth factor, replacing some or all of the first cell culture medium with a second cell culture medium having a second amount of growth factor and further culturing the at least one stem cell in the second cell culture medium, the second amount of growth factor being less than the first amount, and collecting a quantity of the second cell culture medium after a culture duration, wherein the quantity of the second cell culture medium contains a cell culture byproduct effective to treat a mammalian insult or injury. In another embodiment, the method further comprises the step of processing the quantity of the second cell culture medium using a process selected from the group consisting of centrifugation, concentration, fractionation, lyophilization, and freeze-drying, to create a processed product.

In at least one embodiment of a method of producing a stem cell conditioned media of the present disclosure, the method comprises the steps of culturing at least one stem cell in a first cell culture medium comprising EGM2MV and having a first amount of growth factor, the at least one stem cell selected from the group consisting of a adipose stem cell, a mesenchymal stem cell, a pluripotent stem cell from skeletal muscle, a brain stem cell, a common pluripotent stem cell, and a human progenitor cell derived from a mesenchymal stem cell, replacing some or all of the first cell culture medium with a second cell culture medium selected from the group consisting of BME and EBM-2, the second cell culture medium having a second amount of growth factor and further culturing the at least one stem cell in the second cell culture medium, the second amount of growth factor being less than the first amount, collecting a quantity of the second cell culture medium after a culture duration, and processing the quantity of the second cell culture medium using at least one process selected from the group consisting of centrifugation, concentration, fractionation, lyophilization, and freeze-drying, to create a processed product, wherein the processed product comprises at least one factor capable of exerting effective protection of cells comprising neural tissues to treat a mammalian neural injury or insult, the at least one factor selected from the group consisting of at least one angoigenic factor and at least one antiapoptotic factor. In an additional embodiment, the method further comprises the step of administering the cell culture byproduct to a patient having the mammalian insult or injury to treat the mammalian neural injury or insult.

In at least one embodiment of a stem cell conditioned medium of the present disclosure, the stem cell conditioned medium comprises a cell culture supernatant containing at least one factor capable of exerting effective neuroprotection to treat a mammalian (human and/or animal) neural injury or insult, the cell culture supernatant produced by culturing at least one mammalian adipose stem cell to produce the at least one factor. In another embodiment, the cell culture supernatant is produced by culturing at least one mammalian adipose stem cell in a first cell culture medium and later removing some or all of the first cell culture medium and further culturing the at least one mammalian adipose stem cell in a second cell culture medium. In yet another embodiment, the second cell culture medium comprises a growth factor-free basal medium. In an additional embodiment, the first cell culture medium comprises a first amount of growth factor, wherein the second cell culture medium comprises a second amount of growth factor, and wherein the second amount is less than the first amount. In yet an additional embodiment, the cell culture supernatant is collected after the at least one mammalian adipose stem cell has been cultured in the second cell culture medium.

In at least one embodiment of a stem cell conditioned medium of the present disclosure, the at least one factor is selected from the group consisting of at least one angoigenic factor and at least one antiapoptotic factor. In an additional embodiment, the at least one factor capable of exerting effective neuroprotection is capable of protecting against mammalian neuronal cell death. In yet an additional embodiment, the cell culture supernatant is concentrated to a concentration selected from the group of at least 50-fold, between 50-fold and 100-fold, at least 100-fold, between 100-fold and 250-fold, and at least 250-fold. In another embodiment, the cell culture supernatant is fractionated to remove substances less than a specified kDa range selected from the group consisting of less than about 5 kDa, less than about 10 kDa, less than about 20 kDa, less than about 30 kDa, less than about 40 kDa, less than about 50 kDa, and greater than about 50 kDa. In yet another embodiment, the cell culture supernatant is acted upon using a process selected from centrifugation, concentration, fractionation, lyophilization, and freeze-drying.

In at least one embodiment of a stem cell conditioned medium of the present disclosure, the supernatant comprises at least one chemical secretion from the cultured at least one mammalian adipose stem cell. In another embodiment, the at least one factor comprises at least two different factors having a synergistic effect on a target cell and/or organ. In yet another embodiment, the at least one factor comprises a plurality of factors. In an additional embodiment, the at least one mammalian stem cell is cultured in the second cell culture medium under a condition selected from the group consisting of a normoxic condition and a hypoxic condition.

In at least one embodiment of a stem cell conditioned medium of the present disclosure, the mammalian neural injury or insult that at least one factor capable is of exerting effective neuroprotection to treat is selected from the group consisting of a chronic injury, an acute injury, a central nervous system injury, a peripheral nervous system injury, and a neurodegenerative disorder. In an additional embodiment, the mammalian neural injury or insult is selected from the group consisting of Parkinson's disease, Alzheimer's disease, amyotrophic lateral sclerosis, multiple sclerosis, cerebral palsy, peripheral neuropathy, Huntington's disease, epilepsy, encephalomyelitis, encephalitis, inflammation, a spinal cord injury, a brain injury, and cerebral hypoxia.

In at least one embodiment of a stem cell conditioned medium of the present disclosure, the stem cell conditioned medium comprises a cell culture supernatant containing at least one factor capable of exerting effective neuroprotection to treat a mammalian neural injury or insult, the cell culture supernatant produced by culturing at least one mammalian adipose stem cell in a first cell culture medium, later removing some or all of the first cell culture medium and further culturing the at least one mammalian adipose stem cell in a second cell culture medium, and fractionating the cell culture supernatant to remove substances less than a specified kDa range to produce the at least one factor.

In at least one embodiment of a stem cell conditioned medium of the present disclosure, the stem cell conditioned medium comprises a supernatant containing at least one factor, the supernatant obtained by culturing at least one mammalian adipose stem cell in a first cell culture medium, switching the cell culture medium to a substantially growth factor-free second cell culture medium, and collecting the supernatant containing the at least one factor after switching the cell culture medium to the growth factor-free second cell culture medium.

In another embodiment, the cell culture supernatant is concentrated to a concentration selected from the group of at least 50-fold, between 50-fold and 100-fold, at least 100-fold, between 100-fold and 250-fold, and at least 250-fold. In yet another embodiment, the cell culture supernatant is fractionated to remove substances less than a specified kDa range selected from the group consisting of less than about 5 kDa, less than about 10 kDa, less than about 20 kDa, less than about 30 kDa, less than about 40 kDa, less than about 50 kDa, and greater than about 50 kDa.

In at least one embodiment of a method of treating a mammalian (human or animal) patient having a neuronal injury or insult of the present disclosure, the method comprises the step of administering a therapeutically-effective dose of a stem cell conditioned medium to a mammalian patient, the stem cell conditioned medium comprising a cell culture supernatant containing at least one factor capable of exerting effective neuroprotection to treat a mammalian neural injury or insult. In another embodiment, the neural injury or insult is selected from the group consisting of a chronic injury, an acute injury, a central nervous system injury, and a peripheral nervous system injury. In yet another embodiment, the acute injury is selected from the group consisting of a cerebral hypoxia, a spinal cord injury, a brain injury, and inflammation. In an additional embodiment, the central nervous system injury is selected from the group consisting of a brain injury and a spinal cord injury.

In at least one embodiment of a method of treating a mammalian patient having a neuronal injury or insult of the present disclosure, the neural injury or insult comprises a neurodegenerative disorder. In an additional embodiment, the neurodegenerative disorder is selected from the group consisting of Parkinson's disease, Alzheimer's disease, amyotrophic lateral sclerosis, multiple sclerosis, cerebral palsy, peripheral neuropathy, Huntington's disease, epilepsy, encephalomyelitis, encephalitis, a spinal cord injury, a brain injury, and cerebral hypoxia. In yet an additional embodiment, the neural injury or insult comprises a hypoxia-ischemia of the brain selected from the group consisting of neonatal cerebral hypoxia and adult cerebral hypoxia. In another embodiment, the step of administering is performed by administering a therapeutically effective dose of a stem cell conditioned medium to a mammalian patient selected from the group consisting of a neonatal patient, a child, an adolescent, and an adult patient.

In at least one embodiment of a method of treating a mammalian patient having a neuronal injury or insult of the present disclosure, the step of administering is performed by systemically administering a therapeutically effective dose of a stem cell conditioned medium to a mammalian patient. In another embodiment, the systemic administration is selected from the group consisting of injection administration and intravenous administration. In yet another embodiment, the step of administering is performed by locally administering a therapeutically effective dose of a stem cell conditioned medium to a mammalian patient at or near a site of neural injury or insult. In an additional embodiment, the local administration is selected from the group consisting of interarterial administration, intravenous intraparenchymal administration, intrathecal administration, and interperitoneal administration.

In at least one embodiment of a method of treating a mammalian patient having a neuronal injury or insult of the present disclosure, the step of administering is performed to treat a mammalian neural injury or insult by treating neural cells in vivo that are at risk for hypoxia induced neuronal death. In an additional embodiment, the step of administering is performed to treat a mammalian neural injury or insult by treating cerebral tissues damaged by hypoxia. In yet an additional embodiment, the step of administering is performed to treat a mammalian neural injury or insult by stimulating neural cell regeneration. In another embodiment, the cell culture supernatant is produced by culturing at least one mammalian adipose stem cell to produce the at least one factor.

In at least one embodiment of a method of treating a mammalian patient having a neuronal injury or insult of the present disclosure, the method comprises the step of administering a therapeutically-effective dose of a stem cell conditioned medium to a mammalian patient, the stem cell conditioned medium comprising a cell culture supernatant containing at least one factor capable of exerting effective neuroprotection to treat a mammalian neural injury or insult selected from the group consisting of a chronic injury, an acute injury, a central nervous system injury, a peripheral nervous system injury, and a neurodegenerative disorder.

In at least one embodiment of a method of treating a mammalian patient having a neuronal injury or insult of the present disclosure, the method comprises the step of administering a therapeutically-effective dose of a medium containing at least one factor derived from a mammalian stem cell to a mammalian patient to treat a mammalian neural injury or insult. In another embodiment, the mammalian stem cell comprises a human mammalian stem cell, and wherein the mammalian patient comprises a human patient, and wherein the human mammalian stem cell was obtained from the human patient. In yet another embodiment, the mammalian stem cell comprises an animal mammalian stem cell, and wherein the mammalian patient comprises an animal patient, and wherein the animal mammalian stem cell was obtained from the animal patient.

BRIEF DESCRIPTION OF THE DRAWINGS

FIG. 5A: untreated CGN (control). FIG. 5B: cultures exposed to LK (5 mM) BME for 24 h. FIG. 5C cultures exposed to LK (5 mM) media with 30% ASC Conditioned Media for 24 h. Data are from a representative experiment repeated twice with similar results.

FIG. 14a: normal, FIG. 14b: ischemia-treated with BME, FIG. 14c: ischemia treated following 24 h post treatment with ASC Conditioned Media. Note the moderate damage in the hippocampus ipsilateral to carotid ligation in animals (compare FIG. 14a vs. FIG. 14b) and the significant protection by ASC Conditioned Media (FIG. 14b vs. FIG. 14c). Rectangle indicates the lesion site in the left hippocampus. The area of tissue in the hippocampus ipsilateral to the lesioned hemisphere was compared in the same animal with the area of tissue remaining in the matching brain region contralateral to unlesioned hemisphere. The percentage area loss was then determined in each animal, and data are presented as the mean plus or minus SEM for each group. ASC Conditioned Media 24 hours after hypoxia "significantly" protects against hippocampal volume loss induced by ischemic injury (73±3 vs. 90±1, n=2/group, one-way ANOVA, *p<0.05). FIG. 14d: data showing percent of remaining tissue volume in lesioned vs. unlesioned hemisphere for H-I and H-I+SCM.

DETAILED DESCRIPTION

Figure 1:
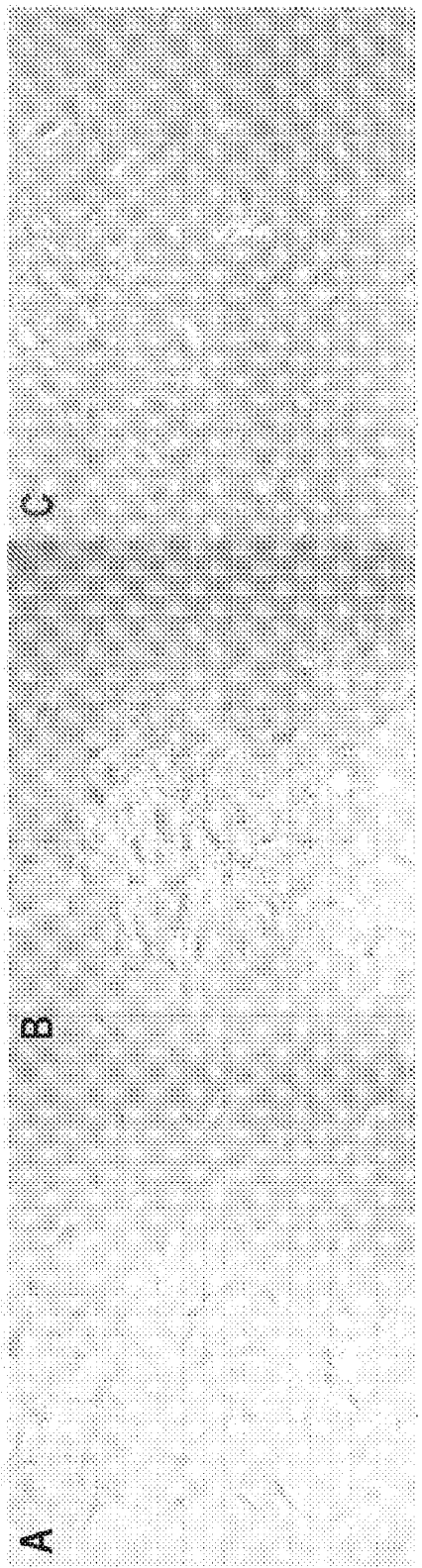
FIG. 1: Phase contrast micrographs of (A) human, (B) mouse, and (C) rat grown in EGM2MV.

For the purposes of promoting an understanding of the principles of the disclosure, reference will now be made to the embodiments illustrated herein and specific language will be used to describe the same. It will nevertheless be understood that no limitation of the scope of the disclosure is thereby intended.

As used herein, a therapeutically effective dosage or amount of a compound is an amount sufficient to affect a positive effect on a given medical condition. The affect, if not immediately, may, over period of time, provide a noticeable or measurable effect on a patient's health and well being.

According to one aspect of the present disclosure, it has been found that when ASCs are cultured in vitro, the ASCs secrete a combination of angiogenic and antiapoptotic factors and/or additional compounds (either as single factors, or in combination with one another) in relative concentrations and combinations that have been shown to exert effective neuroprotection in a variety of mechanistically distinct neuronal death pathways. As a result, according to one embodiment, a therapeutically effective dose of ASC secretions from in vitro culture is administered to prevent or counteract a chronic or acute neural injury or insult.

In particular, according to at least one embodiment, it was found that media used to culture and/or maintain ASCs in vitro has the unexpected characteristic of protecting neural tissue and/or encouraging regeneration from stimuli-induced damage when administered to a patient in a therapeutically effective dosage. This media, or extracts thereof, appears to inhibit critical neuronal death pathways due to the presence of several complementary neuroprotective factors which combine to limit neuronal death and/or stimulate regeneration of neural cells in vitro as well as in vivo in the context of neural insult, although the mechanism is not entirely understood. Further, fractions of media conditioned by ASCs are a source of various factors that either alone or in combination with one another have shown an ability to affect neuronal cells that are subject to acute or chronic injury. Accordingly, the ASC conditioned media has been shown to be an excellent source of material useful for producing, concentrating, and isolating a broad spectrum combination of compounds in relative percentages and forms that effect a therapeutic effect when administered to an individual suffering from a neural insult, including central nervous system or peripheral nervous system injuries that may be chronic or acute in nature. Further, ASC conditioned media has been shown to be an excellent source of material useful for producing, concentrating, and isolating individual compounds, or groups of compounds, that have been shown to protect neuronal cells from death, damage and insult and/or to cause regeneration thereof.

For example, the ASC conditioned media and/or fractions and concentrations thereof have proven effective to treat or prevent various disorders that involve hypoxia-ischemia (H-I) of the brain including neonatal or adult H-I-induced encephalopathy, stroke and neurodegenerative disorders, and such treatments do not carry the same risk of rejection as that shown by injecting foreign stem cells into a patient, since at least one embodiment does not inject any cells whatsoever into a patient. Further, application of ASC conditioned media and/or fractions and concentrations thereof can be used to treat chronic or acute injuries in the peripheral nervous system, central nervous system, and/or spinal cord in either neonatal individuals, children, or adults.

It will be appreciated that other stem cells or pluripotent cells may be utilized, such as other mesenchymal stem cells (MSC), which are found in the stroma of different tissues throughout the body. Human MSCs (including ASCs) are characterized by the surface marker profile of lin−/CD45−/c-kit−/CD90+. Further, in one embodiment, appropriate stem cells display the CD34+ positive at the time of isolation, but lose this marker during culturing. Therefore the full marker profile for one stem cell type that may be used according to the present application is lin−/CD45−/c-kit−/CD90+/CD34. In another embodiment utilizing mouse stem cells, the stem cells are characterized by the Sca-1 marker, instead of CD34, to define what appears to be a homologue to the human cells described above, with the remaining markers remaining the same. It will be appreciated that other stem cells with similar marker profiles could be used, such as the pluripotent stem cell from skeletal muscle that was identified by Case et al (Annals of NY Acad Sci. vol. 1044:183-200). Case indicates that these cells appear to exist in the adipose and brain theorize that these are the same stem cell that resides in many different organs. They have termed these cells common pluripotent stem cells (CoPSC), but other stem cells could be used, with the exception of hematopoietic stem cells. This would also include progenitor cells that derive from MSCs.

The process for producing the ASC conditioned media is further outlined below, as is the method for using the media or its fractions or distillates to treat nervous system insults or neurodegenerative conditions. While the term "ASC conditioned media" is used throughout, it is understood that the same processes will apply to production of similar media through other stem cells, but that adipose stem cells are used for exemplary purposes.

I. Process for Producing ASC-Conditioned Media

A. Isolation and Expansion of Adipose Stem Cells

Figures 2A, 2B:
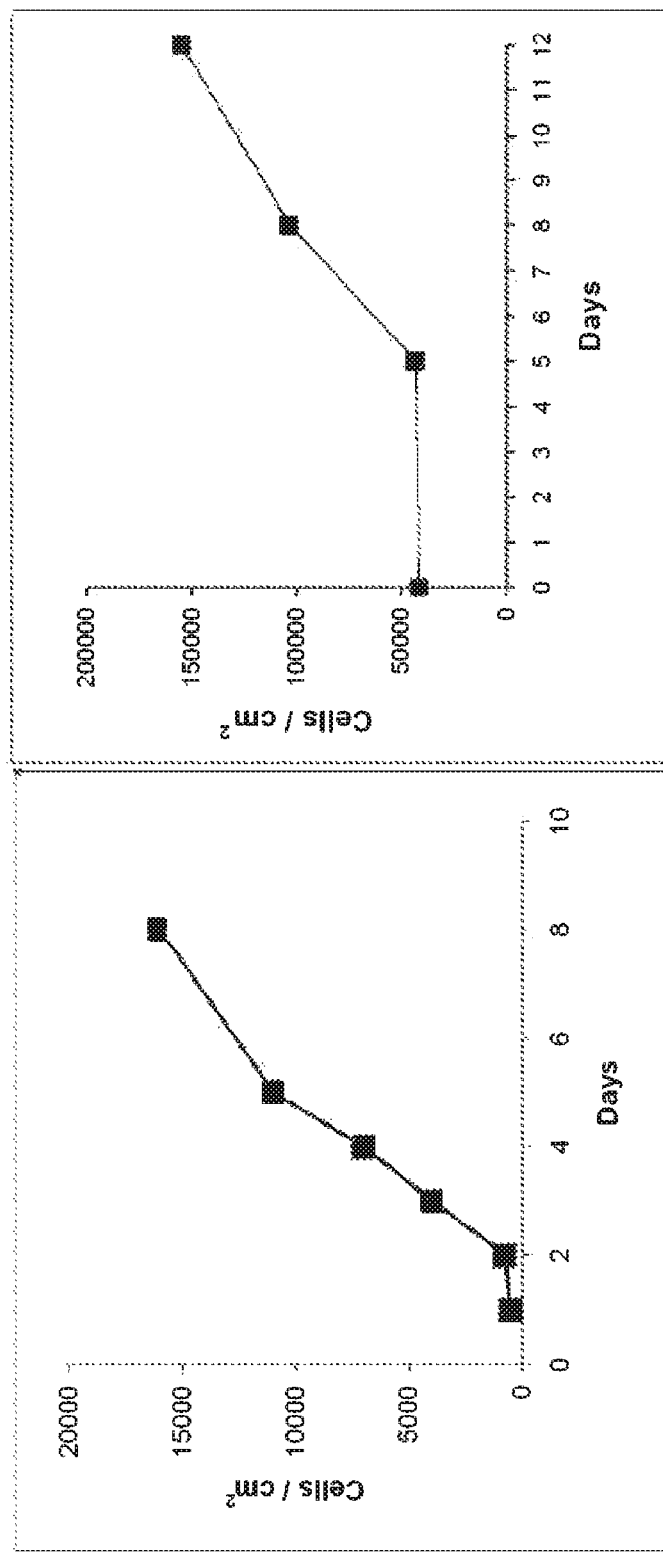
FIG. 2A and FIG. 2B: In vitro expansion of human (FIG. 2A) and mouse (FIG. 2B) ASCs.

To isolate human ASCs, lipoaspirates (250-500 ml) were obtained from patients undergoing elective liposuction procedures and processed essentially according to Zuk et al. ASCs were plated at 1,000-10,000 cells/cm$^2$. Most ASCs attach to the flask and, when cultured in EGM2MV media for example, can be multiplied 50-fold in 8 days (FIG. 1 and FIGS. 2A and 2B) with their growth rate decreasing when they reach confluency. FIG. 2B demonstrates the expansion of murine ASCs following their isolation using similar protocols. Similar growth data has been obtained with rat ASCs as shown in portion C of FIG. 1.

These experiments demonstrate that ASCs are readily isolated and rapidly expanded ex vivo from relatively small amounts of adipose tissue, thus laying the groundwork for using autologous ASCs in research and clinical settings. As discussed further below, neuroprotective studies suggest that 30% of culture media replaced by the culture media from $10^8$ to $10^9$ autologous cells exerts significant neuroprotective effects on different neurodegenerative models.

B. Preparation of ASC-Conditioned Media

Figure 3:
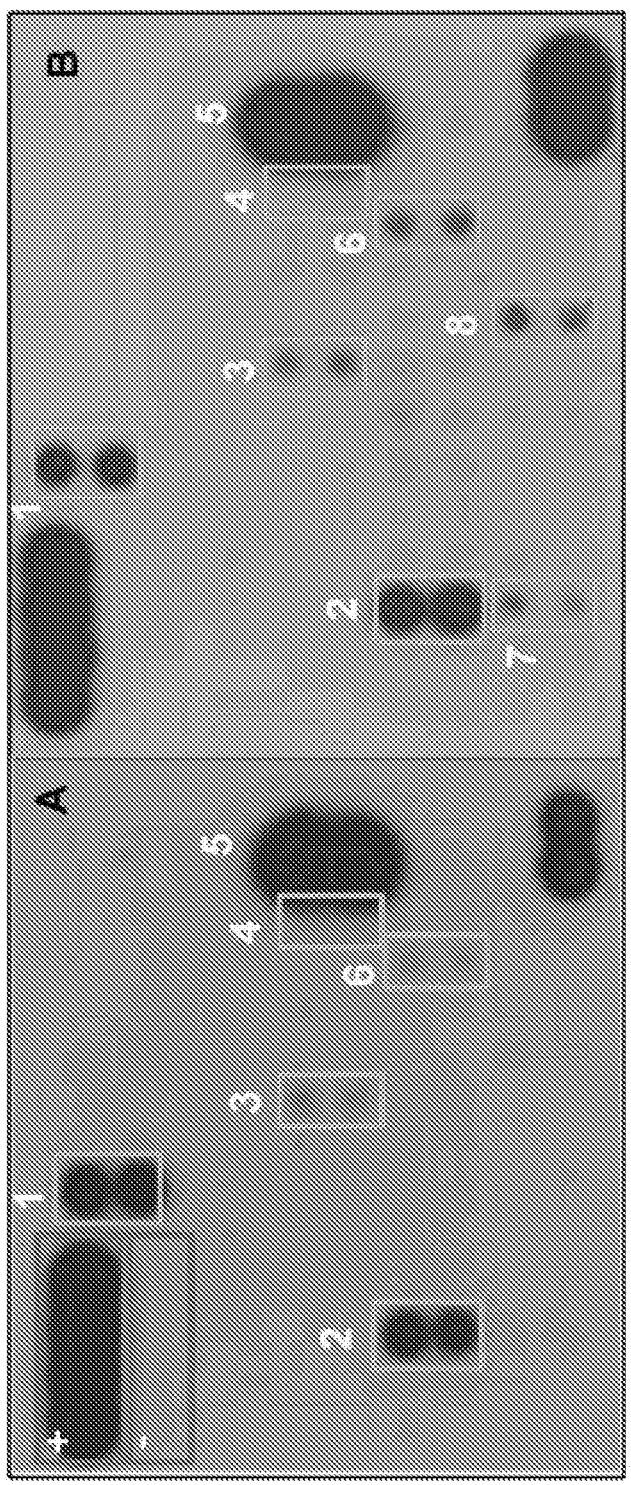
FIG. 3: Profile of cytokines expressed by human ASCs cultured under normoxia (A) or hypoxia (B). Conditioned media was applied to a RayBio antibody array VII and developed for visualization. Numbers refer to antibodies (in duplicate) for specific proteins. A "+" or "−" sign signifies positive or negative controls, respectively. The proteins (with detection limits in pg/ml) are: 1, angiogenin (10); 2, MCP-1 (3); 3, IL-1ralpha☐ (10); 4, IL-5 (1); 5, IL-6 (1); 6, MIP-3a (100); 7, SCF (10); and 8, TNF-beta (1000).
Figure 4:
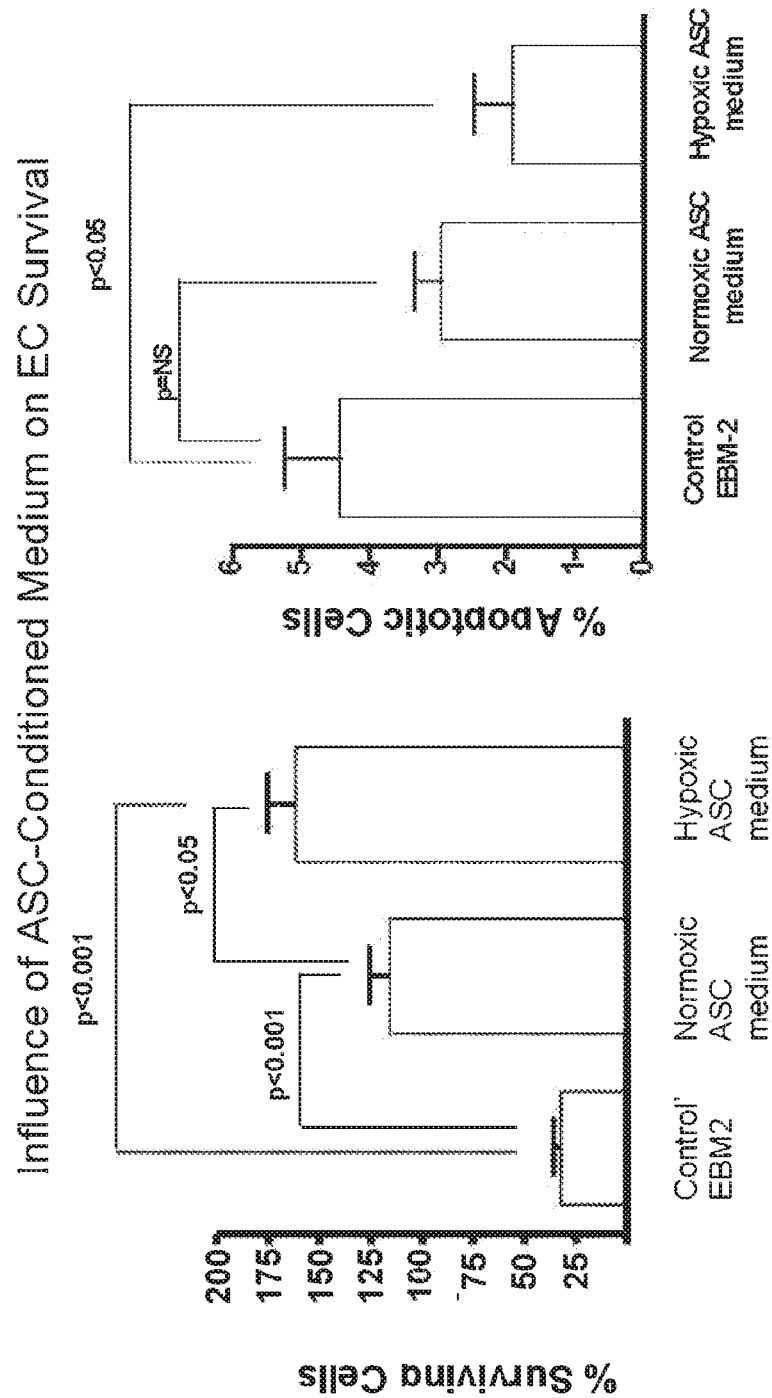
FIG. 4: Influence of ASC-Conditioned Medium on endothelial cell ec Survival and prevention of apoptosis.
Figure 5A:
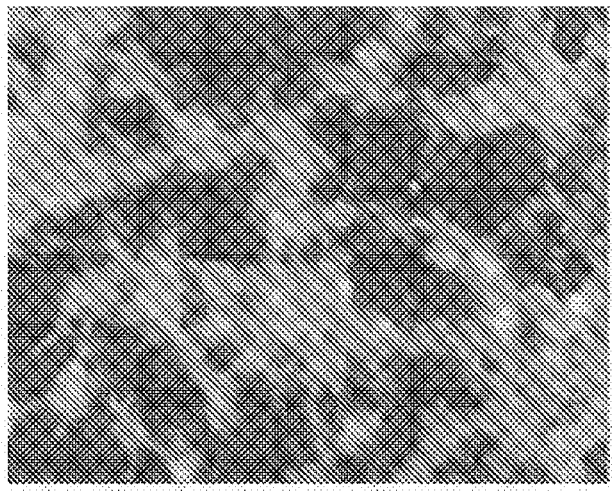
FIG. 5A, FIG. 5B, and FIG. 5C: Conditioned media from ASCs (stromal cell-conditioned medium: ASC Conditioned Media) protects CGN neurons against potassium (5 mM)-induced apoptosis. The rat ASCs were cultured in EGM2MV media to confluence, and then switched into basal media Eagle (BME with 5 mM $K^+$, Invitrogen) for 24 hours. The conditioned media (ASC Conditioned Media) were collected from the ASCs culture and subsequently added to the regular BME (5 mM $K^+$) at volumes equivalent to 30% of the total media volume. The BME with ASC Conditioned Media was then added to rat CGN cultures. Viable neurons was quantified by counting fluorescein (green) positive cells which result from the de-esterification of fluorescein diacetate (FDA, Sigma, 10 μg/ml, 5 min) by living cells. Propidium iodide (PI, Sigma, 5 μg/m, 5 min), which interacts with nuclear DNA of dead cells, producing a red fluorescence, was used to identify dead neurons (Du, 1997a).
Figure 5B:
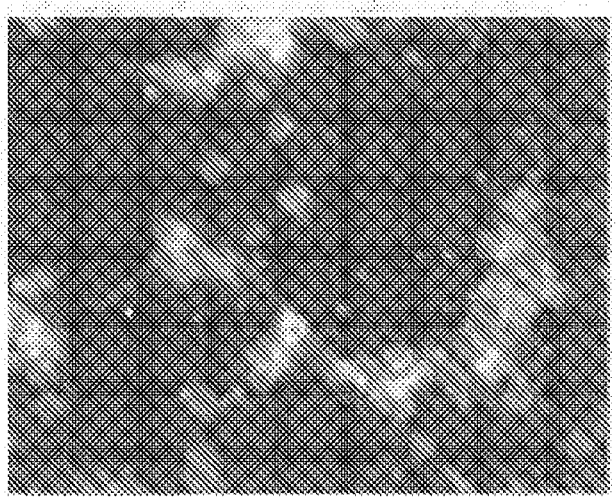
Figure 5C:

The ASCs were cultured in EGM2MV medium to confluence, and then switched into growth-factor free basal media (EBM-2, Clonetics) for conditioning in either normoxic or hypoxic conditions for 72 hours. Cell supernatants were collected and subsequently assayed for cytokines using a RayBio array VI and VII. FIG. 3 displays the findings of array VII, and indicate that in addition to the pluripotency of ASCs, the endocrine or paracrine potential of ASCs may have significant therapeutic relevance. Testing as shown that ASCs delivered to the CNS in the setting of degeneration as a result of ischemia due to stroke in this case may be able to protect neurons from death processes as well as enhance angiogenesis by both differentiating into vascular phenotypes, and by recruiting resident mature vascular endothelial cells to integrate into the nascent vascular network. More importantly, in experiments directed to determining the overall biological effect of the ASC conditioned media, human microvascular endothelial cells were exposed to the media conditioned by ASCs incubated in (1) normoxic conditions, (2) hypoxic conditions, and (3) unconditioned media as a control. As shown in FIG. 4, after 4 days, exposure to ASC-normoxic media resulted in an 80% increase in HMVEC number, while the ASC-hypoxic media resulted in a 160% increase in HMVEC number as compared to the control. These significant increases confirm the potential of ASC conditioned media to promote growth or survival of other cells in their vicinity.

C. Isolation of Components in ASC Conditioned Media by Fractionation

Our studies illustrate that ASCs Conditioned Media during culture plays a critical role in protecting neurons from injurious stimuli. Defined protein fractions (<10 k, 10-30 k, 30-50 k, and >50 k) from the conditioned media have been evaluated with respect to their ability to block neuronal death in specific, well-defined in vitro models. Data shows that the passage number of the ASCs as well as various environmental stimuli influence the level and composition of factor secreted into the media and the resulting neuroprotective efficacy of conditioned media.

Neuronal death is mediated by complementary neuronal death pathways in distinct neurodegenerative models, and may be limited in each model by distinct trophic factor(s) by ASCs within the conditioned media. Neuroprotective factors the conditioned medium, such as VEGF and HGF, can be selected for by selectively altering the activity of present factors through the addition of inactivating antibodies, or conversely, by adding purified recombinant proteins to fractionated supernatants.

Evaluation of the Neuroprotective Capacity of Different Fractions of Media from ASCs in Different in vitro Neuronal Death Models.

Factors secreted into the media during culture of ASCs potently protect neurons from injury stimuli associated with specific neuronal death pathways. Defined fractions of conditioned media from human, murine and rat ASCs, at different passages and subjected to hypoxia or normoxia, have been enriched by >50-fold in order to evaluate increase the potency of neuroprotection and to enable detection of low abundance proteins by proteomic assays. Once the conditioned medium is enriched, it is optionally fractionated by, for example, size exclusion and then can be concentrated. Optionally, ASC Conditioned Media is simply concentrated and/or fractionated. In this manner, concentrations of the ASC Conditioned Media can be manipulated.

According to another embodiment, ASCs derived from human, mouse or rat adipose tissue, as described above are evaluated by flow cytometry to confirm that they are CD34+, CD90, c-kit−, CD31−, CD45− and, in the case of murine cells, Sca1+. The cells are then plated in DMEM/F12 with 10% FBS with no additional growth factors added; and EGM/2MV (Cambrex) is used. The resulting ASC Conditioned Media is thereafter applied for treatment or prevention of neural injury.

ASC Conditioned Media is enriched and size fractionated supernatants can be further fractionated using a centrifugal filter device (10K, 30K, and 50K Centriplus, Amicon, Mass.). Centriplus molecular weight filters can provide an 100-fold sample enrichment and can easily be used to enrich samples by 50 to 250-fold using a 10 kDa. Neuroprotective factors in different fractions of the supernatant are likely to be predominantly within the ranges of <10 kDa, 10-30 kDa, 30-50 kDa, and >50 kDa. It is known that growth factors, for example, have a large size difference (such as GCSF 20 kDa BDNF 27 kDa EPO 34 kDa VEGF 45 kDa, and NGF 116 kDa) based on size separation and will segregate in different molecular weight fractions. Optional steps include collecting and fractionating supernatants from fresh or passaged ASCs grown under normoxic or hypoxic conditions, and using these fractions for neuroprotection in LK/HK, glutamate, H2O2, ODG, 6OHDA, and MPP+ CGN models.

D. Delivery, Timing, and Dosing of ASC Conditioned Media

1. Delivery

Unlike cell therapies that inject stem cells at the point of injury, the process for treatment of injured nervous system cells, or cells prone to injury or neurodegenerative diseases does not require localized injection. Rather, it will be appreciated that since no living cells, which may die if used systemically, are being utilized, that a wide array of delivery systems may be used to ensure that the ASC conditioned media, its fractions, concentrations, or distillations may be delivered systemically, via injection, intravenously, or otherwise. Optionally, the ASC conditioned media may be delivered locally at the site of injury. For example, the ASC Conditioned Media may be delivered interarterially, intravenously intraparenchemally, intrathecally, or interperitonally.

2. Timing

In certain models, such as in the H-I model, that at 24 h following induction of hypoxia, the Blood Brain Barrier ("BBB") is disrupted, allowing peptide penetration. Additionally, some growth factors, such as GCSF and IGF-1, can penetrate into the brain immediately after H-I treatment. Identifying key factors for neuroprotection, initially concentrated conditioned ASC Conditioned Media were used. 7 day old pups underwent will undergo H-I, followed by iv injections of 1-10 μl of 250-fold concentrated rat ASC conditioned supernatant fractions or a cocktail with defined growth factors at 2, 8 and 24 hours post surgery. As a control, animals were injected with the same amount of BME media.

The first few hours following H-I are believed to be the most critical for neuronal death resulting from direct effects of the insult. Secondary damage, triggered by inflammation, occurs after 48 hours. Given the prolonged period in which damage occurs, it may be beneficial to repeat dosing in order to effectively block neuronal death. Additionally, the ASC conditioned media or fraction thereof may have function to regenerate neurons derived from stem cells. Accordingly, the ASC Conditioned Media or fraction thereof is optionally administered at an optimized concentrate at least once daily for at least one day, at least 2 days, or at least 3 days following insult (such as H-I insult, onset of neurodegeneration, or surgery). Further optionally, due to the neural protection shown when ASC conditioned media or a fraction thereof is administered prior to insult, the ASC conditioned media may be optionally administered at least one day, at least 2 days, or at least 3 days prior to the insult or surgery.

3. Dosage

According to one aspect of the present application, a therapeutic dose of the ASC conditioned is delivered to an individual. In one embodiment, a defining characteristics of the ASC conditioned media are naturally-derived factors secreted into the medium during fermentation of ASCs. This conditioned medium (CM) possesses the qualities of being able to prevent damage to neurons due (a) ischemic events, (b) induction of cell-death processes (apoptosis), (c) excitotoxity, (d) oxidation, or (e) neuron-specific damaging agents. In vitro assays for each would be (a) oxygen-glucose deprivation (OGD), (b) Low K model, (c) glutamate excitotoxicity, (d) hydrogen peroxide, and (e) 6-hydroxy-dopamine toxicity of dopaminergic neurons at a therapeutic dose.

According to one embodiment, the ASC-CM is concentrated at least 50 fold, at least 100-fold, at least 200 fold, or at least 1000-fold. Optionally, the concentrated ASC-CM is fractionated through a size exclusion resin or membrane to remove substances less than 5 kDa, less than 10 kDa, less than 20 kDa, less than 30 kDa, less than 40, kDa, or less than 50 kDa. The concentrated ASC-CM is then optionally stabilized to protect degradation or loss of components. According to one exemplary embodiment of dosing, 800 MICROLITERS/kg and up to 4000 MICROLITERS/kg have demonstrated efficacy in animal models when delivered as a single bolus to the jugular vein, either before or after carotid artery ligation. However, according to alternative embodiments, dosing of about 200 to 10,000 microliters per kg, about 600 to 2,000 microliters per kg, and about 1,000 to 1,200 microliters per kg may be delivered as a single bolus as a therapeutic dose.

Figure 19:
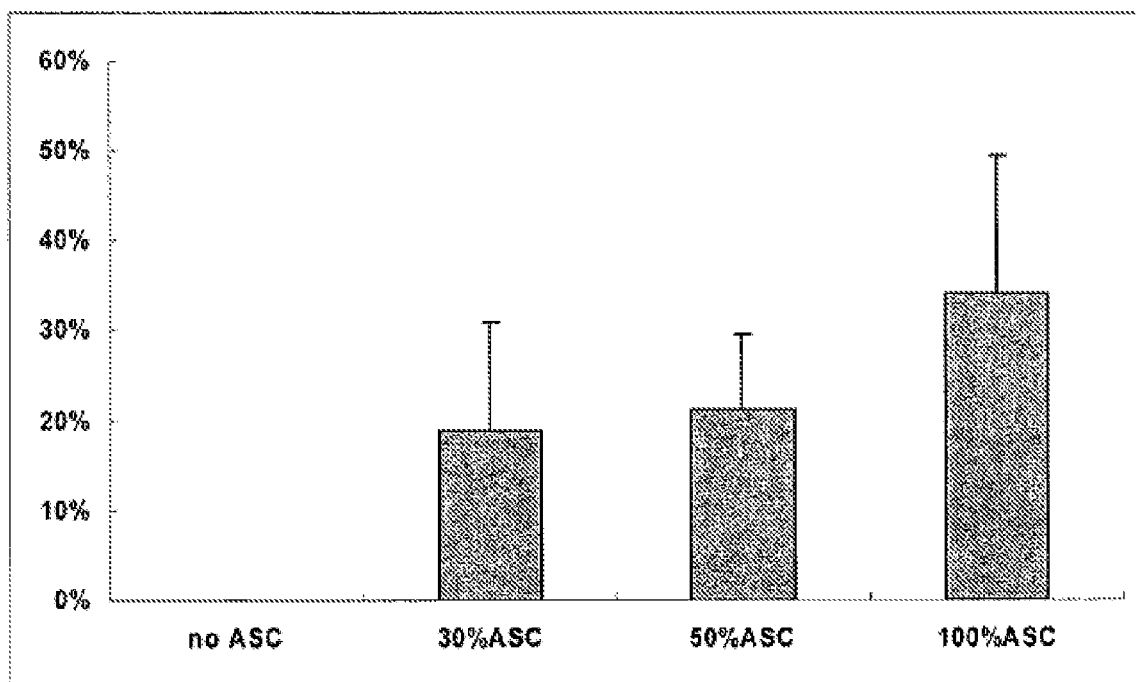
FIG. 19 displays the results of PC12 cells were cultured in DMEM containing 10% FBS for 3 days, then starved in BME medium without FBS for 24 hours. Various percentages of the medium was exchanged for an equivalent volume of ASC-CM, as indicated in FIG. 19.

Turning to FIG. 19, according to another embodiment of the present disclosure, PC12 cells were cultured in DMEM containing 10% FBS for 3 days, then starved in BME medium without FBS for 24 hours. Various percentages of the medium was exchanged for an equivalent volume of ASC conditioned media, as indicated on the figure above. The cells were cultured for 8 days in these media, which were replaced with freshly made equivalent media every second day. The number of cells that formed a neuronal phenotypes were quantitated using a phase-contrast microscope. The results are expressed as the mean percentage of neurite-bearing cells±sd, indicating that the ASC conditioned media induces differentiation to neurite-bearing cells.

II. Experimental Support of Efficacy Across Neuronal Degenerative Models

Figure 16:
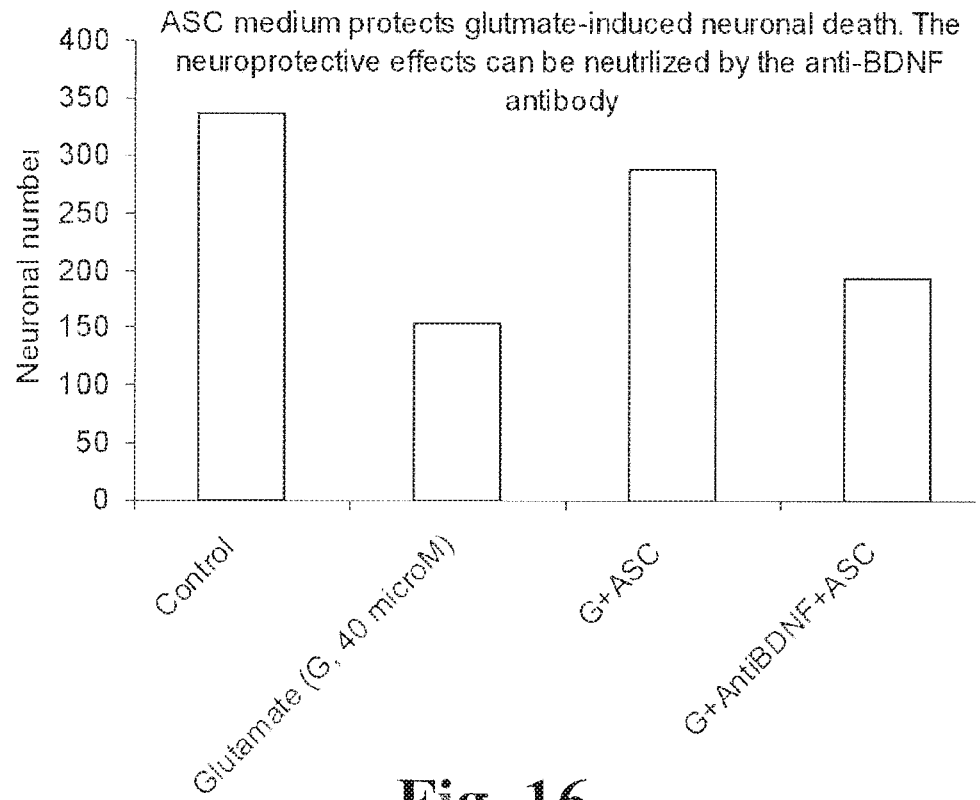
FIG. 16: As expected, in inactivation of a single factor present in ASC Conditioned Media, which is known to limit damage due to a specific insult, significantly reduces the ability of ASC Conditioned Media to protect against the specific damaging agent. Injury was induced in CGN by exposure to 40 µM glutamate as described above. ASC Conditioned Media, protected the CGN from damage (G+ASC). Pretreatment of ASC Conditioned Media with an anti-BDNF antibody that neutralizes BDNF activity significantly, but not totally, reduced the ability of ASC Conditioned Media to protect CGN (G+antiBDNF+ASC). Conversely, it would not be expected that BDNF activity would protect neutrons from injury due to other damaging agents or conditions, such as OGD, oxidation (e.g., $H_2O_2$), or toxins (E.g., MPP).

It will be appreciated that treatment of neural tissue according to certain embodiments disclosed in the present application were evaluated against several in vitro neuronal degenerative models to demonstrate the effectiveness of the treatment and composition with regard to multiple and varying types of damage that can induce neuronal death. These models are well established tools for the study of the CNS and peripheral nervous system related diseases, disorders and injuries. (Ni, 1997; Du, 1997a; Du, 1997b; Dodel, 1998; Dodel, 1999; Du, 2001; Lin, 2001; Lin, 2003). The use of these various models, which produce reasonable similes of prevalent human diseases, are particularly powerful tools for the study of the broad range of effectiveness of the ASC Conditioned Media because each model is defined by distinct mechanisms involving varied pathways of degeneration. Furthermore, it is well known to those knowledgeable in the art that interference of the distinct mechanisms involved in cellular degeneration is limited to discrete factors and, furthermore, that individual factors that act on one mechanism have no effect on others. Individual trophic factors can modify only discrete degenerative pathways or mechanisms. Therefore, a specific factor would be expected to protect neurons from degenerative mechanisms involved in specific neuronal death models, but would not provide any protection in models involving damaging agents that induce unrelated mechanism. Therefore, a single factor is unable to protect neurons from all neuronal death mechanisms. However, a mixture of factors, as is present in ASC Conditioned Media, would provide the full complement of factors, acting individually or in combination, necessary to block all degenerative mechanisms causing cell death. In FIG. 16 it is shown that ASC Conditioned Media possesses a factor (BDNF) that protects neurons from glutamate-induced death. Neutralization of this factor greatly, but not totally, reduces cell death in this model. Conversely, tests in an in the mechanistically distinct LK/HK death model demonstrated by neutralization of BDNF that this factor is not important for modifying mechanisms leading to neuron death in this model. Therefore, BDNF as an individual factor, as example, would not protect neurons from all mechanisms causing neuron death.

Detailed descriptions of the major neuronal death pathways, the involvement of each pathway in the models used in this study and the relevance of each model to human disorders is described in greater detail as follows below.

A. Mitogen-Activated Protein Kinase

Mitogen-activated protein (MAP) kinases are widely expressed serine-threonine kinases that mediate important regulatory signals in cells. Three major groups of MAP kinases exist: the extracellular signal-regulated (ERK) kinase family, the c-Jun $NH_2$-terminal kinase (JNK) family, and the p38 MAP kinase (p38) family. The members of the different MAP kinase groups participate in the generation of various cellular responses including gene transcription, induction of cell death, maintenance of cell survival, malignant transformation, and regulation of cell-cycle progression (Widmann, 1999). The ERK-pathway is activated in response to several cytokines and growth factors and primarily mediates mitogenic and anti-apoptotic signals (Chang, 2001). There are three isoforms of JNK. At least one of the $JNK_{1-3}$ MAP kinases is activated in response to stress and growth factors and similarly mediates signals that regulate apoptosis, cytokine production (inflammation), and cell-cycle progression (Davis, 2000). JNK signaling has been shown to be involved in transient hypoxia-induced apoptosis in developing brain neurons (Chihab, 1998) and targeted deletion of $JNK_3$ protected adult mice from brain injury after cerebral ischemia-hypoxia (Kuan, 2003). Additionally, blockade of JNK rescues neurons against potassium deprivation-induced CGN death (Xifro, 2005) and glutamate-induced neurotoxicity (Munemasa, 2005). p38 MAP kinase was discovered as a major protein activated by LPS in macrophages and has been characterized as the target for anti-inflammatory drugs that inhibit IL-1 and TNF biosynthesis in monocytes (Lee, 1994; Han, 1994). Members of the p38 MAP kinase group are primarily activated by stress stimuli, but also during engagement of various cytokine receptors by their ligands (Lee, 1994; Lu, 1999; Rincon, 1998; Wysk, 1999). The function of p38 kinases is required for the generation of various activities including regulation of apoptosis and cell cycle arrest, induction of cell differentiation, as well as cytokine production and inflammation (Dong, 2002). p38 MAP kinase also phosphorylates and/or modulates the activity of a number of transcriptional factors involved in cytokine responses including STAT1, IFNγ regulatory factor-1, and NF-κB (Beyaert, 1996; Vanden Berghe, 1998). Recently, it has been reported that inhibition of p38 MAP kinase significantly inhibits NO— (Ghatan, 2000; Oh-hashi, 1999; Du, 2001), glutamate-(Kawasaki, 1997) and possibly hypoxia-ischemia-induced neuronal death (Hee, 2002).

Many of the genes responsible for apoptotic cell death, including those underlying neuronal apoptosis, have now been identified and named as caspases (Du, 1997a). Apoptotic cell death is often mediated by a caspase cascade. Although many stimuli exist, the final phases of apoptosis are executed by a few common effector caspases. Mitochondria appear to provide a link between the initiator caspases and the downstream effector caspases. In non-neuronal cells, mitochondria have been shown to accelerate activation of caspases by releasing pro-apoptotic molecules, such as cytochrome c (Yang, 1997). MAP kinases such as JNK and p38 have been reported to regulate caspase 3-mediated cell death (Harada, 1999; Cheng, 2001). However, it has also been reported that c-Jun and p38 MAP kinases do not induce neuronal death through the caspase-3 pathway (Sang, 2002; Roth, 2000). We have identified the involvement of caspase 3 in cytochrome c-mediated, glutamate- (Du, 1997a), MPP- (Du, 1997b), 6-hydroxdopamine- (Dodel, 1999), and potassium-deprivation-induced neurotoxicity (Ni, 1997). Additionally, it has been suggested that caspase 3 plays a role in the rat H-I model (Turmel, 2001). Further, it has been documented that cytochrome c and caspase 3 have more important function in the premature brain than the mature brain (Xu, 2004).

B. LK Induced CGN Apoptosis Model of Neuronal Cell Death

To induce apoptosis under the LK CGN model disclosed by Ni in 1997, CGN maintained in BME with 25 mM potassium are switched to regular BME (5 mM potassium) without serum and CGN (>50%), which induces apoptosis within 24 h (Ni, 1997). This model was one of the first to be established, and is still widely used in studies of neuronal apoptosis in the primary cerebellar granule neuron (CGN) culture system, although its precise relevance to the disease remains unclear (D'Mello, 1993; Dudek, 1997, Ni, 1997).

In the developing rodent cerebellum, granule neurons undergo developmentally regulated apoptosis peaking at the end of the first week of postnatal life (Wood, 1993). Granule neurons cultured from rats or mice around this time of development undergo cell death in culture unless they are provided with extrinsic survival factors. Maximal survival is produced by the combination of growth factors typically provided by serum together with neuronal activity which is induced by high extracellular concentrations of potassium chloride that depolarize the membrane and induce activation of voltage-sensitive calcium channels (D'Mello, 1997; Padmanabhan, 1999; Miller, 1996; Catterall, 2000). The signaling mechanisms by which growth factors and neuronal activity promote the survival of CGN are beginning to be characterized. Protein kinase cascades figure prominently in the control of neuronal survival. The ERK1/2-Rsk, phosphatidylinositol 3-kinase-Akt, and ERK5 protein kinase signaling pathways play critical roles in mediating the survival of CGN upon exposure to the neurotrophin brain-derived neurotrophic factor (Bonni, 1999; Shalizi, 2003). The phosphatidylinositol 3-kinase-Akt signaling pathway plays a central role in mediating insulin-like growth factor 1-mediated neuronal survival (Brunet, 2001). Removal of survival factors promotes neuronal apoptosis in part because of inactivity of pro-survival protein kinases. However, deprivation of survival factors also leads to stimulation of other protein kinases that impart an apoptotic signal in neurons. These protein kinases include JNK, p38, Cdc2, and GSK3 (Harada, 1999, Estus, 1994; Xia, 1995; Watson, 1998; Yang, 1997; Donovan, 2002; Konishi, 2002; Konishi, 2003; Mora, 2001).

C. Glutamate Induced Model of Neuronal Cell Death

According to testing protocol for the glutamate induced neuronal death model, neuronal apoptosis or necrosis is induced in CGN with 30-100 µM glutamate or cortical neurons (CN) with 100 µM of NMDA. Glutamate is an excitatory neurotransmitter used throughout the central nervous system and is associated with various brain functions, such as synaptic plasticity, learning, and long-term potentiation (Collingridge, 1989). Its physiological and pathological effects in the CNS are mediated mainly via two types of ionotropic glutamate receptors, the NMDA receptor and the non-NMDA receptor. When present in excessive concentrations glutamate has the potential to induce serious damage and even death of neurons (Lucas, 1957), with N-methyl-D-aspartate (NMDA) receptors located on neuronal cell bodies playing a major role in this excitotoxicity (Rothman, 1987). NMDA receptor activation allows an influx of calcium through both glutamate-activated cationic channels (NMDA) and voltage-gated $Ca^{2+}$ channels activated by a prolonged depolarization (Choi, 1987; Coulter, 1992; Olney, 1971). Although increases in intracellular calcium concentrations are a necessary component of many normal signal transduction pathways, excessive and prolonged rises of $Ca^{2+}$ can lead to mitochondrial membrane dysfunction and cell death (Farber, 1981; Sombati, 1991), induced in part by $Ca^{2+}$-mediated excitotoxicity (Wahlestedt, 1993) and/or failure to regulate cell volume (Pasantes-Morales, 2000). Cell death associated with glutamate neurotoxicity has been suggested to contribute to the devastating effects of a number of serious medical conditions including stroke, persistent seizures of status epilepticus, and neurodegenerative disorders such as Alzheimer's disease, amyotrophic lateral sclerosis, multiple sclerosis, spinal cord injury and Huntington's disease (Choi, 1988; Choi, 1990; Kandel, 1991).

It has been reported that reactive oxygen species (ROS) are generated by activation of the glutamate receptor (Campisi, 2004). Additionally, MAP kinases including JNK and p38 are also implicated in glutamate-induced neuronal apoptosis (Xia, 1995; Chen, 2003). Furthermore, caspase 3 activation appears to play an important role in glutamate neurotoxicity (Du, 1997).

D. Hydrogen Peroxide Induced Model of Neuronal Cell Death

According to the hydrogen peroxide induced death model, we treated CGN with 10 µM of $H_2O_2$ to induced neuronal death (Lin, 2003). It has been suggested that hydrogen peroxide leads to apoptotic neuronal death by involving pro-apoptotic molecules (Wei, 2000), like initiator caspases (See, 2001). Superoxide anions seem to be responsible for the apoptotic cell death of trophic factor-deprived sympathetic neurons (Greenlund, 1995a; b), glutamate-treated cerebellar neurons (Ishikawa, 1999; Satoh, 1998; and Patel, 1996), and hippocampal neurons incubated with xanthine oxidase (Guo, 1999; Ishikawa, 1999). Singlet oxygen has also been involved in apoptotic death in nonneuronal cells mediated by Bid and some members of the MAPK family (Zhuang, 1998). In addition, singlet oxygen has been related to the alterations in the mitochondrial permeability transition pore that occur in several apoptotic death models (Salet, 1997; Moreno, 2001). ROS contributes to the production of peroxynitrites and could also have relevance in induction of apoptotic cell death (Virag, 1998).

E. Nitric Oxide Induced Model of Neuronal Cell Death

Treatment of CGN with 50 µM of sodium nitroprusside (SNP, a NO donor) induces neuronal death (Lin, 2001). Nitric oxide (NO) generated from neuronal nitric oxide synthase (nNOS) and inflammatory inducible isoform of nitric oxide synthase (iNOS) inhibits the mitochondrial respiratory chain in vitro (Clementi, 1998), stimulates neurotransmitter release from synaptosomes (Meffert, 1994) and can cause autocrine excitotoxicity in neuronal cultures (Leist, 1997). NO plays a critical role in neurodegenerative diseases and cerebral ischemia. It has been suggested that excessive production of NO causes these diseases by destroying neurons. The mechanisms proposed for NO-mediated neurotoxicity include inactivation of the mitochondrial respiratory chain (Heales, 1994), S-nitrosylation of glyceraldehyde-3-phosphate dehydrogenase (McDonald and J. Moss, 1993), inhibition of cis-aconitase (Drapier, 1993), activation of poly (ADP-ribose) synthase, and DNA damage (Zhang, 1994), most of which can be mediated by the formation of nitroso compounds by cellular components. Additionally, p38 MAP kinase and cGMP-dependent protein kinase (PKG) have been implicated in NO— induced neuronal apoptosis (Ghatan, 2000; Lin, 2001; Bonthius, 2004).

F. 6-Hydroxy Dopamine Neuronal Model of Neuronal Cell Death

Treatment of CGN or dopaminergic neurons (DA) with 6-hydroxydopamine ("6-OHDA") induces neuronal death (Dodel, 1999). 6-OHDA is a neurotoxin that is specific for catecholamine/dopaminergic neurons (DN) in both the central and peripheral nervous systems. This neurotoxin has been widely used for the Parkinson disease (PD) research. It has been hypothesized that 6-OHDA induces neuronal death possibly via uncoupling mitochondrial oxidative phosphorylation resulting in energy deprivation (Glinka, 1996). Alternatively, 6-OHDA-induced neurotoxicity has been associated with its rapid auto-oxidation at neutral pH, thus producing hydrogen peroxide, hydroxyl and superoxide radicals (Kumar, 1995; Tiffany-Castiglinoi, 1982). Quinones formed during the auto-oxidation of 6-OHDA may undergo covalent binding with nucleophilic groups of macromolecules such as —SH, —$NH_2$, —OH, possibly further enhancing 6-OHDA-induced neurotoxicity (Izumi, 2005). Furthermore, peroxynitrite ($ONOO^-$), which is a potent oxidant formed during the nearly instantaneous reaction of nitric oxide with superoxide anion, has also been found to be involved in 6-OHDA-induced neurochemical effects (Ferger, 2001) and neurotoxicity (Mihm, 2001). Peroxynitrite-mediated protein nitration has been well documented in neurodegenerative disorders including Parkinson's disease (Beckman, 1993; Good, 1996, 1998). We used CGN since CGN undergo cell death as do dopaminergic neurons when exposed to 6-OHDA and MPP (Dodel, 1999; Du, 1997a). Importantly, neuronal death pathways have been better characterized in CGN since this system provides a pure neuronal culture (Dodel, 1999).

G. MPP+ Induced Neuronal Model of Neuronal Cell Death

Treatment of CGN or dopaminergic neurons (DA) with MPP+ induces neuronal death (Du, 2001). MPTP/$MPP^+$-induced neurodegeneration of DAN and CGN is widely used to investigate and characterize the pathogenesis of PD (Du 2001). $MPP^+$ is incorporated into cells via the dopamine transporters and the main targets of $MPP^+$ are the mitochondria, where it inhibits Complex I in the respiratory chain and abolishes oxidative phosphorylation (Tipton, 1993). Although the cerebellum has not been extensively studied as a target for $MPP^+$ neurotoxicity, CGCs are quite sensitive to the toxic effects of $MPP^+$ in vitro (Du, 1997a; Gonzalez-Polo, 2003). The neurotoxic action of this compound is known that $MPP^+$ binds to complex-I of the mitochondrial respiratory chain, causing the inhibition of NAD-linked mitochondrial respiration (Javitch, 1985), the increase in the generation of reactive oxygen species (Akaneya, 1995) and caspase-3 activation (Du, 1997a). It has been also suggested the regulatory effects of $MPP^+$ on the N-methyl-D-aspartate (NMDA)-receptor, inducing the $Ca^{2+}$ entry into the cell (Robinson and Coyle, 1987).

H. Hypoxia-Ischemia Neuronal Model of Neuronal Cell Death

Hypoxic-ischemic (H-I) encephalopathy during the prenatal and perinatal period is a major cause of damage to the fetal and neonatal brain resulting in considerable morbidity and mortality (Wei, 2004). However, currently, there is no effective treatment to prevent the consequences of neonatal H-I in humans. Both rat and mouse in vitro and in vivo models of neonatal H-I have been established for mechanistic study. Hypoxic-ischemic insults can trigger both apoptosis (delayed programmed cell death) and necrosis. It has been reported that young neurons die of necrosis and delayed apoptosis (Northington, 2001), whereas adult neurons usually die of necrosis only (Walton, 1999). This difference is mainly due to the upregulation of NMDA receptors and increased caspase-3 activity in the young brain and these two factors make young neurons particularly vulnerable to H-I injury (Johnston, 2002). Mitochondria appear to play an essential role in determining the fate of cells subjected to hypoxia-ischemia (Gilland, 1998). Disrupted mitochondrial function during H-I can lead to cytochrome c protein release and trigger an activation of caspase 3/other caspase-related apoptotic pathways (Cheng, 1998). Additionally, Calpain and neuroinflammation may also be involved in H-I-induced neuronal injury (Arvin, 2002, Wei, 2004). The prominence of both apoptosis and necrosis in neurodegeneration after H-I in the immature brain suggests that it will be important to better understand the roles and relationships of these processes to develop effective neuroprotective strategies.

I. Oxygen and Glucose Deprivation Neuronal Death Model

The in vitro oxygen and glucose deprivation (OGD) model highly correlates to mechanisms of action in the in vivo H-I model. We culture cortical (CN) or hippocampal (HN) neurons from 1-d pups and after 7-d subject neurons to two hours of hypoxia in media without glucose (see method for details). This model can be used for mechanistic study of in vivo hypoxia-ischemia-induced neuronal injury.

In summary, the table below lists some of the major neuronal death pathways that are involved in the above-mentioned models.

TABLE 1

| Models | LK | Glu | $H_2O_2$ | 6OHDA | MPP | NO | OGD |
|---|---|---|---|---|---|---|---|
| Cell type | CGN | CGN, CN | CGN | CGN, DN | CGN, DN | CGN | CN, HN |
| Necrosis (N) or apoptosis (A) | A | N and A | N and A | N and A | N and A | N and A | N and A |
| Caspase 3 | weak | strong | weak | weak | strong | weak | modest |
| JNK | modest | modest | weak | weak | modest | weak | modest |
| p38 | modest | modest | weak | weak | weak | strong | modest |
| Transcription/translation blocker | strong | weak | weak | weak | weak | weak | weak |
| Antioxidant | weak* | weak* | Strong | Some Strong | Some Strong | Some Strong | modest for some |
| Physiology relevance | Apoptosis model | Ischemia and others | All neurodegenerative disorders | PD | PD | PD and inflammation-related neuronal death | Hypoxia and ischemia |

*Some antioxidants may have neuroprotective functions through non-antioxidant functions.

J. Assessment of Neuroprotective Effects Using Neurodegenerative Models.

The in vitro and in vivo neuronal death models were used to quantify the neuroprotective effect exerted by ASCs conditioned media. These methods were further used to show the efficacy of using various fractions and component of ASC conditioned media to produce significant neuroprotective effects on different neuronal death pathways. These techniques can also be used in vivo neonatal H-I model to examine whether the conditioned medium or factors identified therein can be systemically delivered to exert neuroprotection in vivo.

III. Results of Testing ASC-CM Against Use of Neurodegenerative Models

When the following neurodegenerative models were used by incorporating ASC-CM into in vitro cultures, or according to protocol set forth herein, the following results were noted.

A. ASC Conditioned Media Protects CGN Against Glutamate-Induced Neuronal Death.

Figure 6:
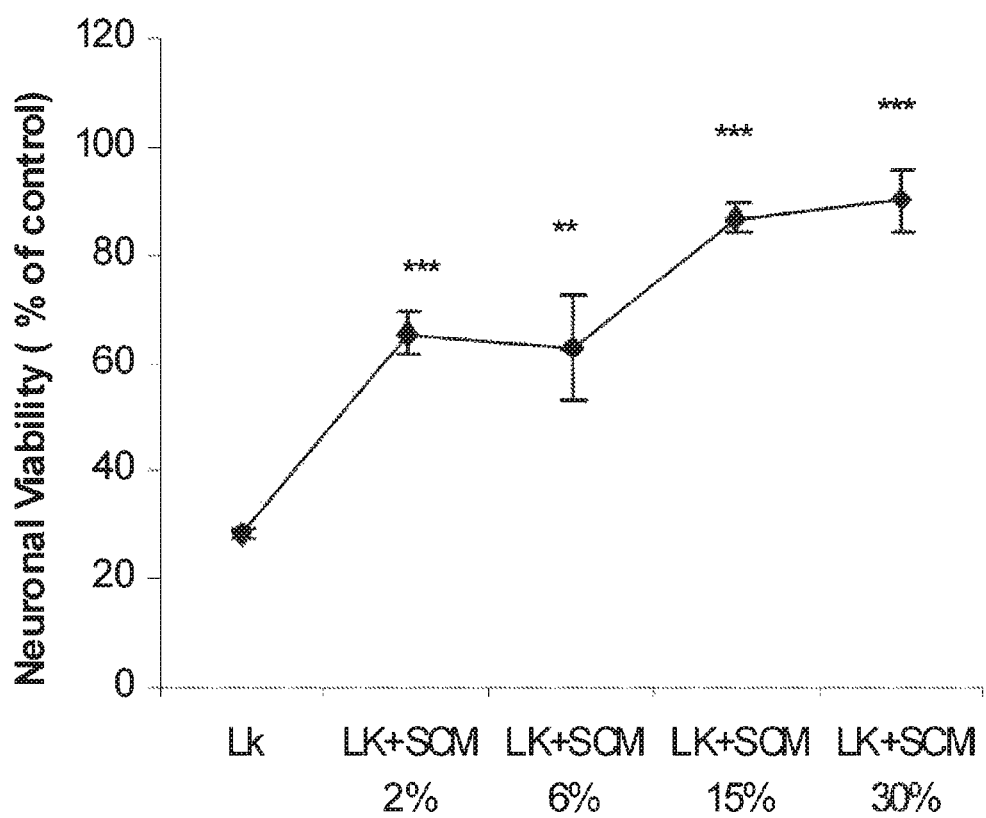
FIG. 6: ASC Conditioned Media protects CGN neurons against LK-induced apoptosis in a dose-dependent fashion. The rat ASC Conditioned Media (2-30% of final vol) was added to the rat CGN cultures following LK treatment. The cultures were then double stained with FDA and PI (as demonstrated in FIG. 5). Data are from a representative experiment repeated twice with similar results.
Figure 7:
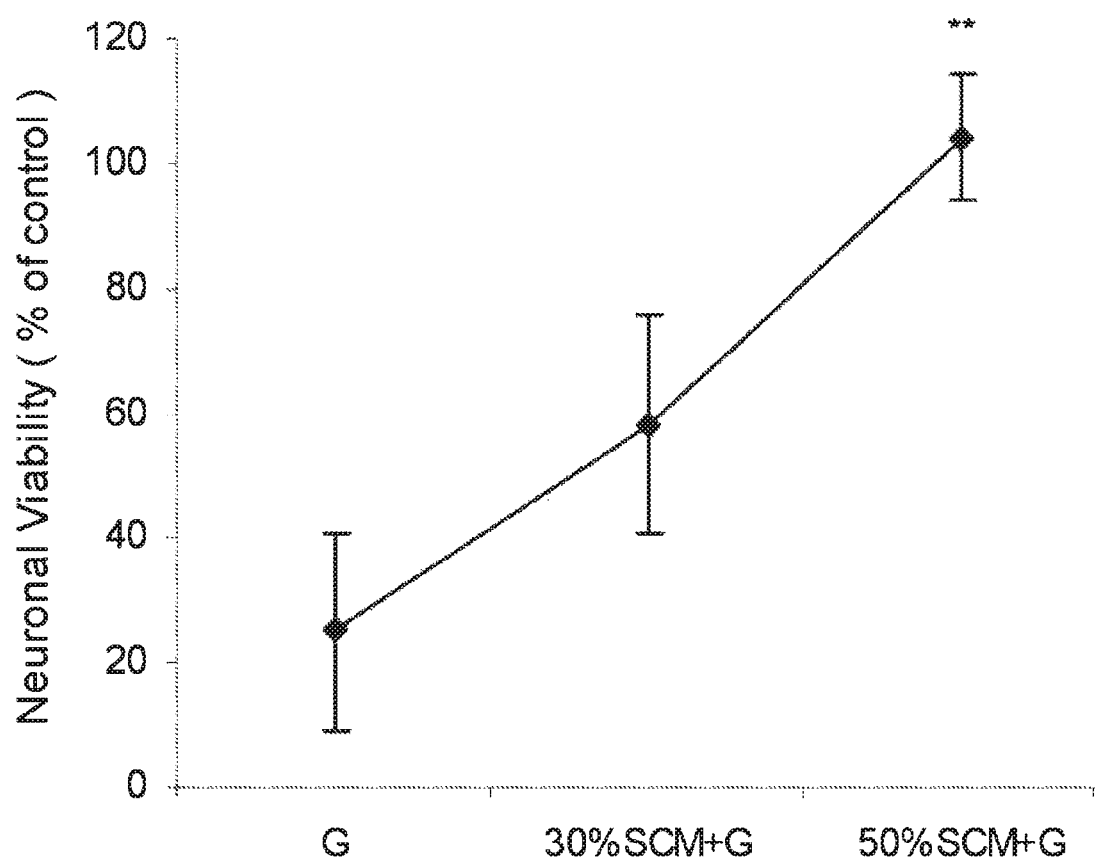
FIG. 7: ASC Conditioned Media protects CGN neurons against glutamate (50 μM)-induced neuronal death. The ASC Conditioned Media was collected and subsequently added into the CGN cultures (30% or 50% replacements) that were then challenged by 50 μM of glutamate. Neuronal viability was quantified by staining neurons with FDA (Du, 1997). G indicates that the CGN were exposed to 50 μM glutamate; SCM+G, CGN exposed to 50 μM glutamate and the indicated percentages of ASC Conditioned Media.
Figure 8:
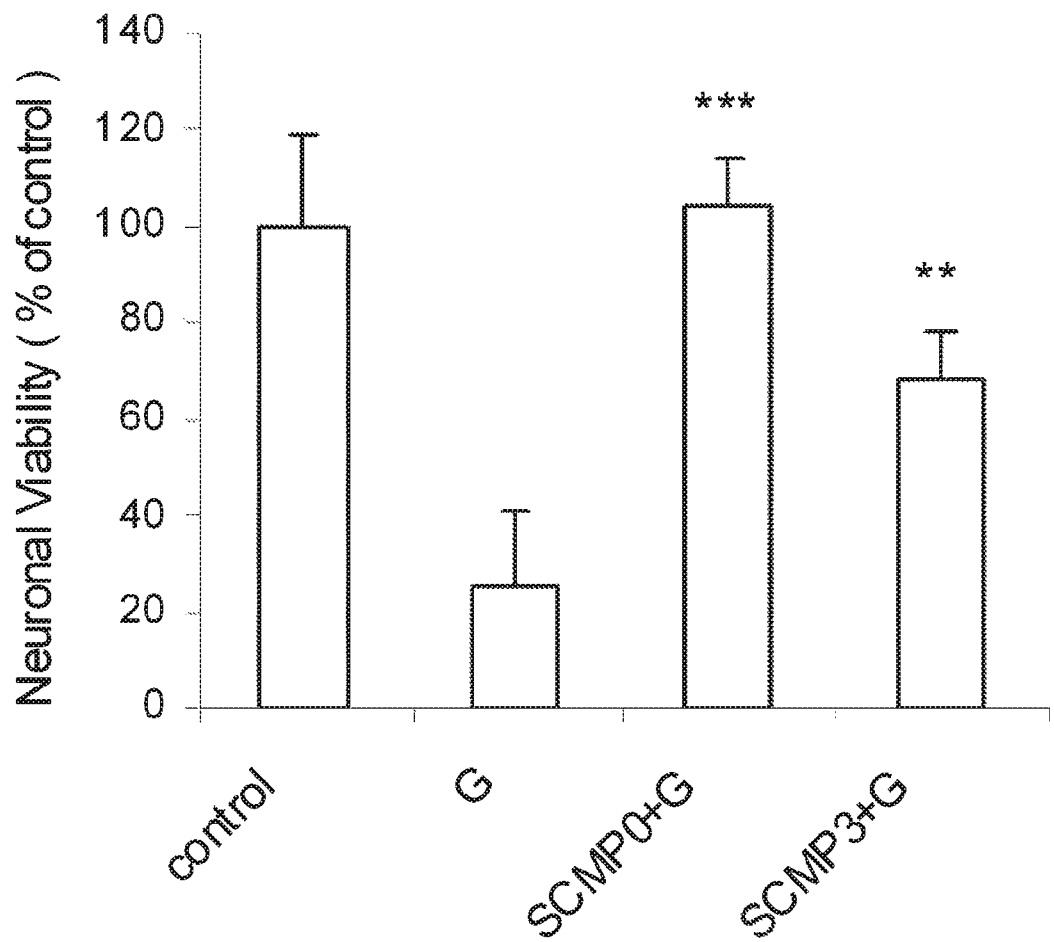
FIG. 8: ASC Conditioned Media collected from fresh (P0) or passage 3 (P3) ASCs protects CGN neurons against glutamate (50 µM)-induced neuronal death differently. The 50% replacement of P0 ASC Conditioned Media exerts a stronger neuroprotective effect than P3 ASC Conditioned Media. Neuronal viability was quantified by staining neurons with FDA (Du, 1997). Control is CGN without 50 µM glutamate exposure; G indicates that the CGN were exposed to 50 µM glutamate; SCMP0+G and SCMP3+G, CGN exposed to 50 µM glutamate and 50% ASC Conditioned Media from cells at P0 or P3, respectively.
Figure 9:
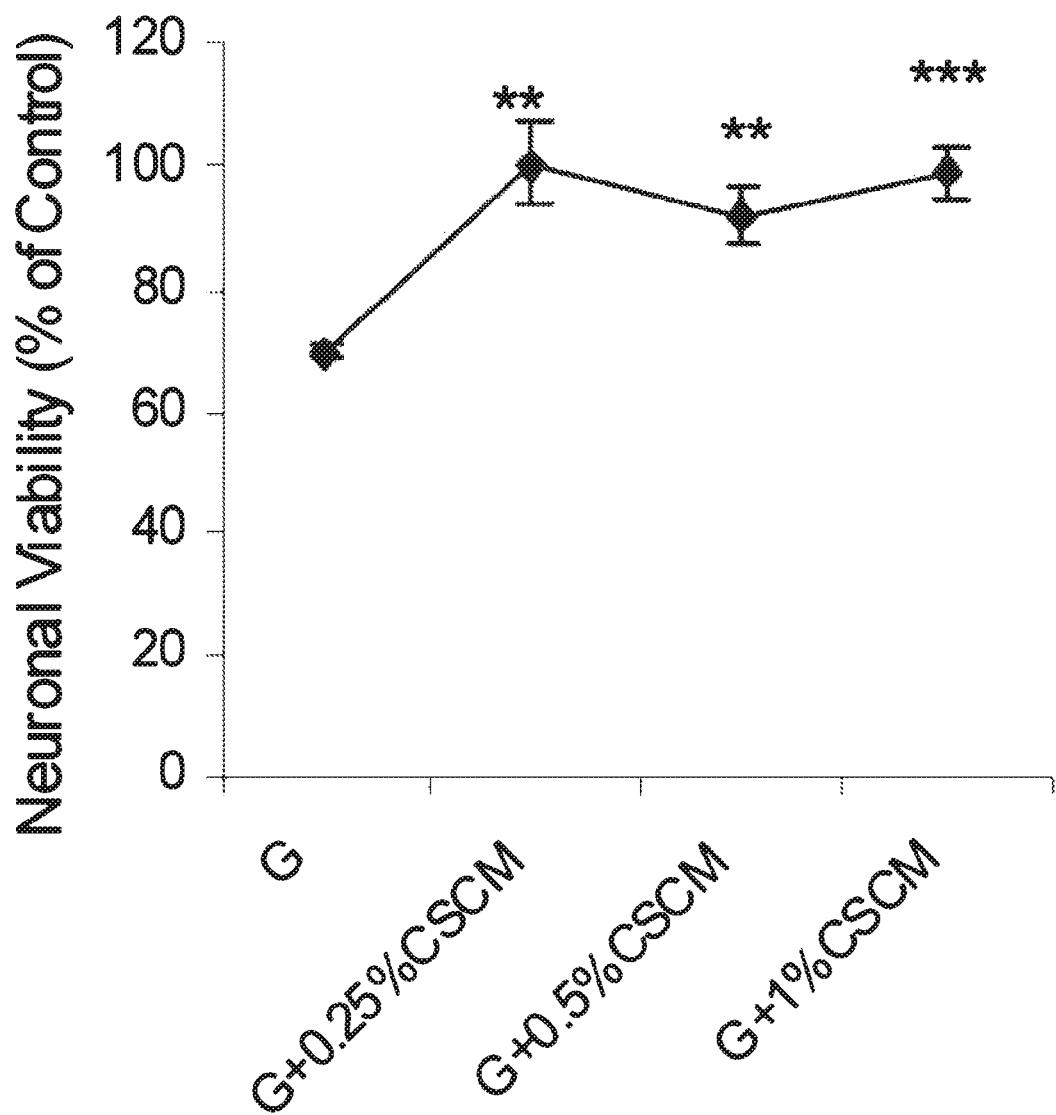
FIG. 9: ASC Conditioned Media collected from fresh ASCs has been enriched 50× using 10K CentriPlus protects CGN neurons against glutamate (50 µM)-induced neuronal death. Addition of 250× enriched ASC Conditioned Media almost completely protects neurons against glutamate toxicity in CGN. Neuronal viability was quantified by staining neurons with FDA (Du, 1997). G indicates that the CGN were exposed to 50 µM glutamate; G+CSCM CGN exposed to 50 µM glutamate and the indicated percentages of 250× Concentrated ASC Conditioned Media.
Figure 10:
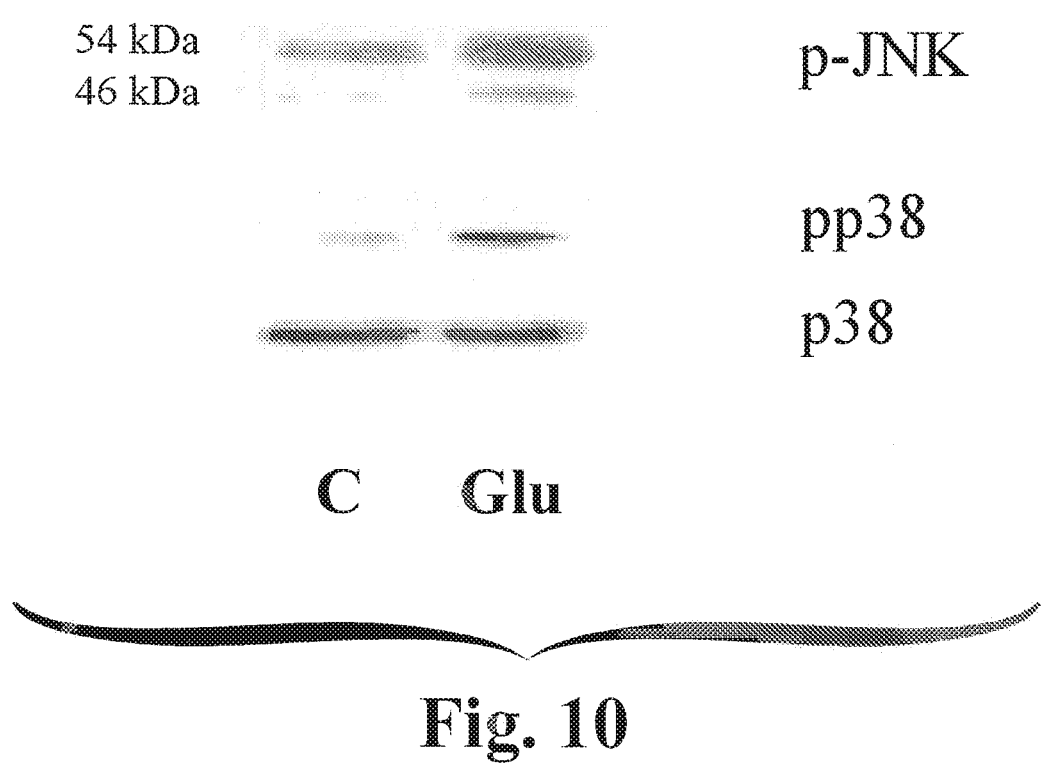
FIG. 10: Glutamate treatments induced JNK and p38 phosphorylation in CGN. Immunoblot analyses were performed with antibodies against phosphorylated JNK and p38 (p-JNK and pp38), and p38 (Santa Cruz). Glutamate treatments increase p-JNK and pp38 by 3 h post-treatment. Note that glutamate treatment fails to alter total p38 expression in the same samples. C=control (no glutamate treatment). Glu=glutamate treatment. Each condition represents 3 samples.
Figure 11:
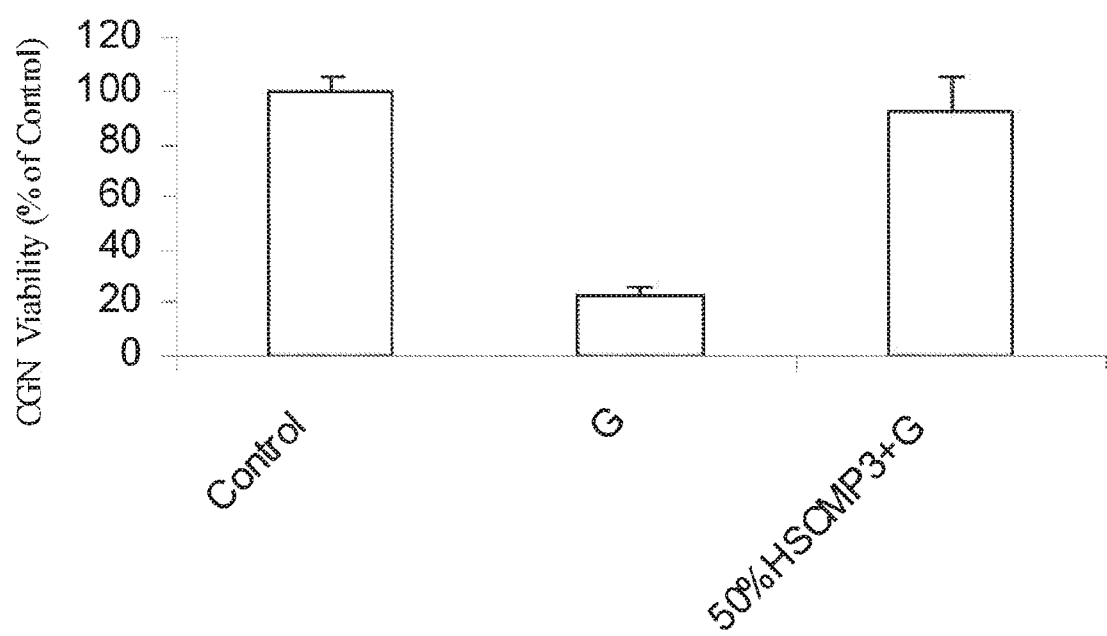
FIG. 11: ASC Conditioned Media collected from P3 human ASCs (HASC Conditioned MediaP3) protects CGN neurons against glutamate (50 µM)-induced neuronal death. The 50% replacement of P3 HSMC exerts a strong neuroprotective effect on rat CGN followed by glutamate treatments. Neuronal viability was quantified by staining neurons with FDA (Du, 1997). Control, CGN without 50 µM treatment; G, CGN exposed to 50 µM glutamate; 50% HSCMP3+G, CGN exposed 50 µM glutamate and 50% ASC Conditioned Media.

Glutamate induces both neuronal necrosis and apoptosis and this in vitro model has been widely used for research of stroke, Parkinson's disease, and Alzheimer's disease (Du, 1997). In order to understand the physiological relevance of ASC Conditioned Media, in the glutamate model was used to test neural cells cultured on media containing ASC Conditioned Media. As shown in FIG. 6, the conditioned medium from ASCs significantly protected neurons against glutamate neurotoxicity. Furthermore, FIG. 7 demonstrates that ASCs which had not been previously cultured ("fresh") produce an ASC conditioned Media that possesses a higher potency in neuroprotection than ASCs that are not fresh. Further, FIG. 8 indicates that ASC Conditioned Media that still retains the protective/regenerative characteristics fractionate by size exclusion chromatography at apparent molecular weights in excess of 10 kDa.

B. Human ASC-Conditioned Media Protects CGN Against Glutamate-Induced Rat Neuronal Death.

Human ASC Conditioned Media was tested in a rat glutamate toxicity model. The results indicate that human ASC Conditioned Media, like that of rat, significantly attenuated glutamate neurotoxicity in rat CGN, suggesting that ASC Conditioned Media induce activity in rat cells. Thus, the rodent model can be useful for assaying the neuroprotective properties of human ASCs.

C. ASC Conditioned Media Protects CGN Against $H_2O_2$-Induced Neuronal Death.

The $H_2O_2$-induced neuronal death model shows the role of free radicals in neurodegeneration. Free radicals have been implicated in almost all types of neurodegenerative processes. Test results shown in FIG. 12 demonstrate that ASC Conditioned Media exerted potent anti-oxidant activity, thereby protecting CGN from oxidative damage and death.

D. ASC Conditioned Media Protects Against OGD-Induced Cortical Neuronal Death.

Figure 13:
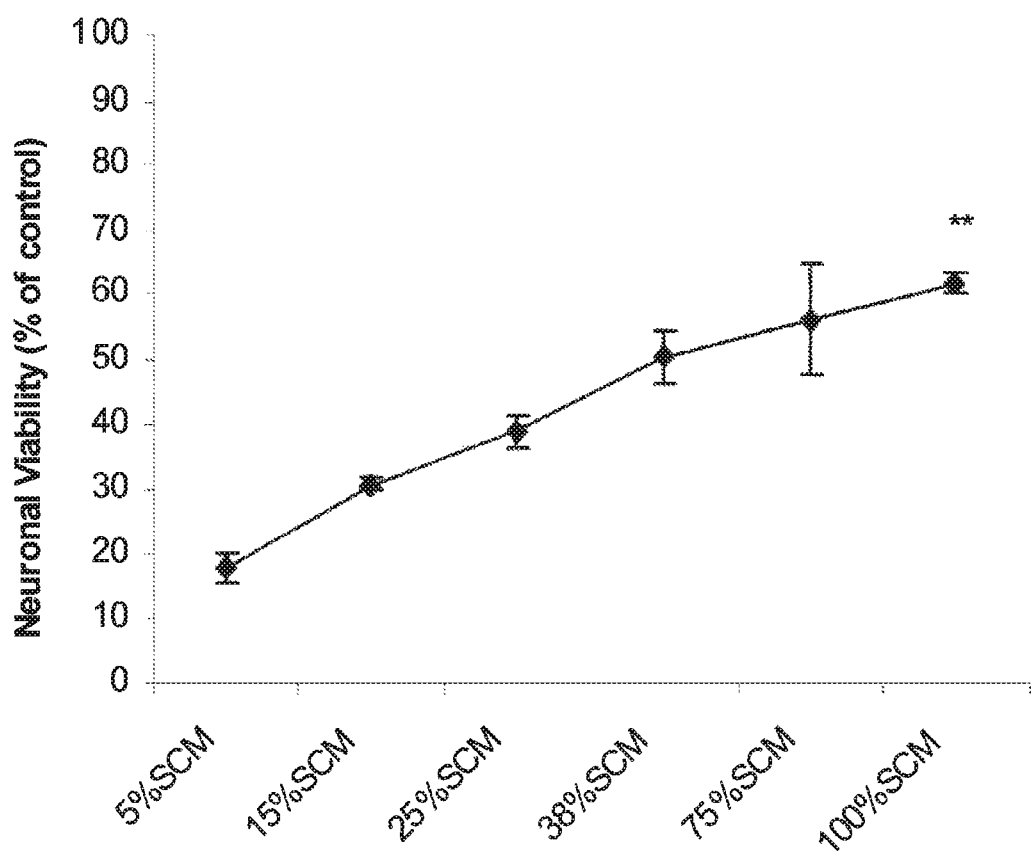
FIG. 13: ASC Conditioned Media treatment improved cortical neuron survival following oxygen and glucose deprivation (OGD) injury. ASC Conditioned Media (added to a final concentration of 5%-100% by replacing the medium) protects cortical neurons in a dose-dependent fashion. SCM, ASC Conditioned Media added at the indicated percentages.
Figure 14A:
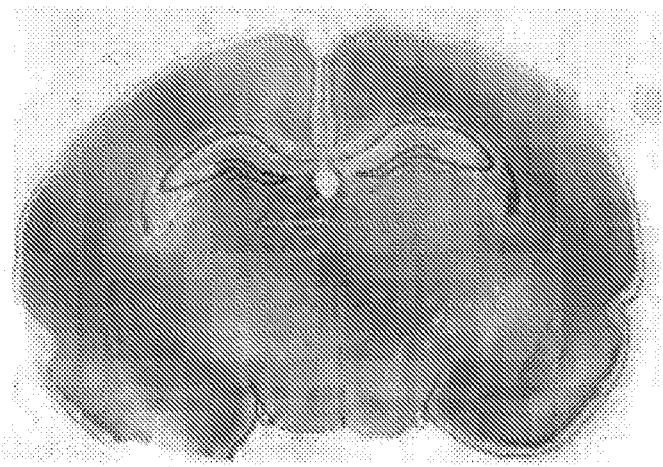
FIG. 14a, FIG. 14b, FIG. 14c, and FIG. 14d: ASC Conditioned Media prevents neuronal loss when administered to neonatal rats at 24 hours following hypoxic-ischemic injury. Representative coronal sections of postnatal day 14 (P14) rat brains demonstrate that 7 days following unilateral (left) carotid ligation and exposure to hypoxia (7%) for 2 hours at P7 (Wei, 2004) with or without treatment with ASC Conditioned Media (10 µl/pup, 24 h following H-I treatments).
Figure 14B:
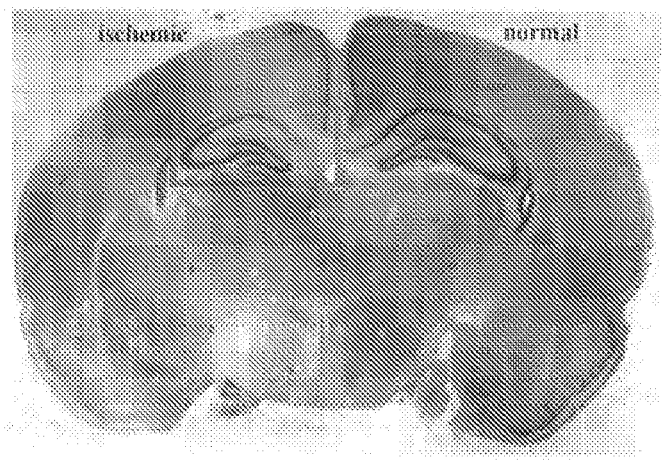
Figure 14C:
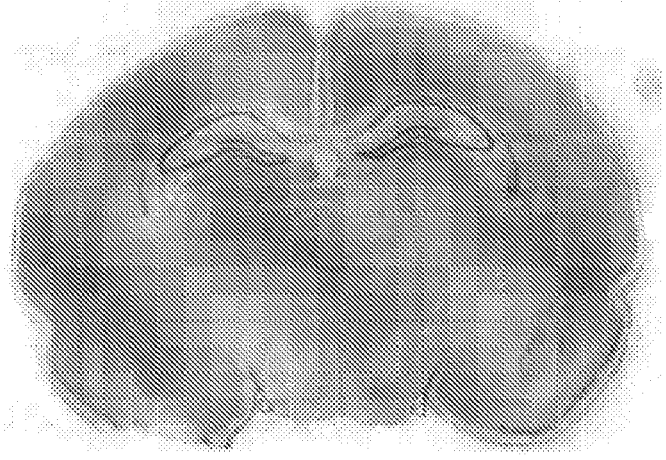
Figure 14D:
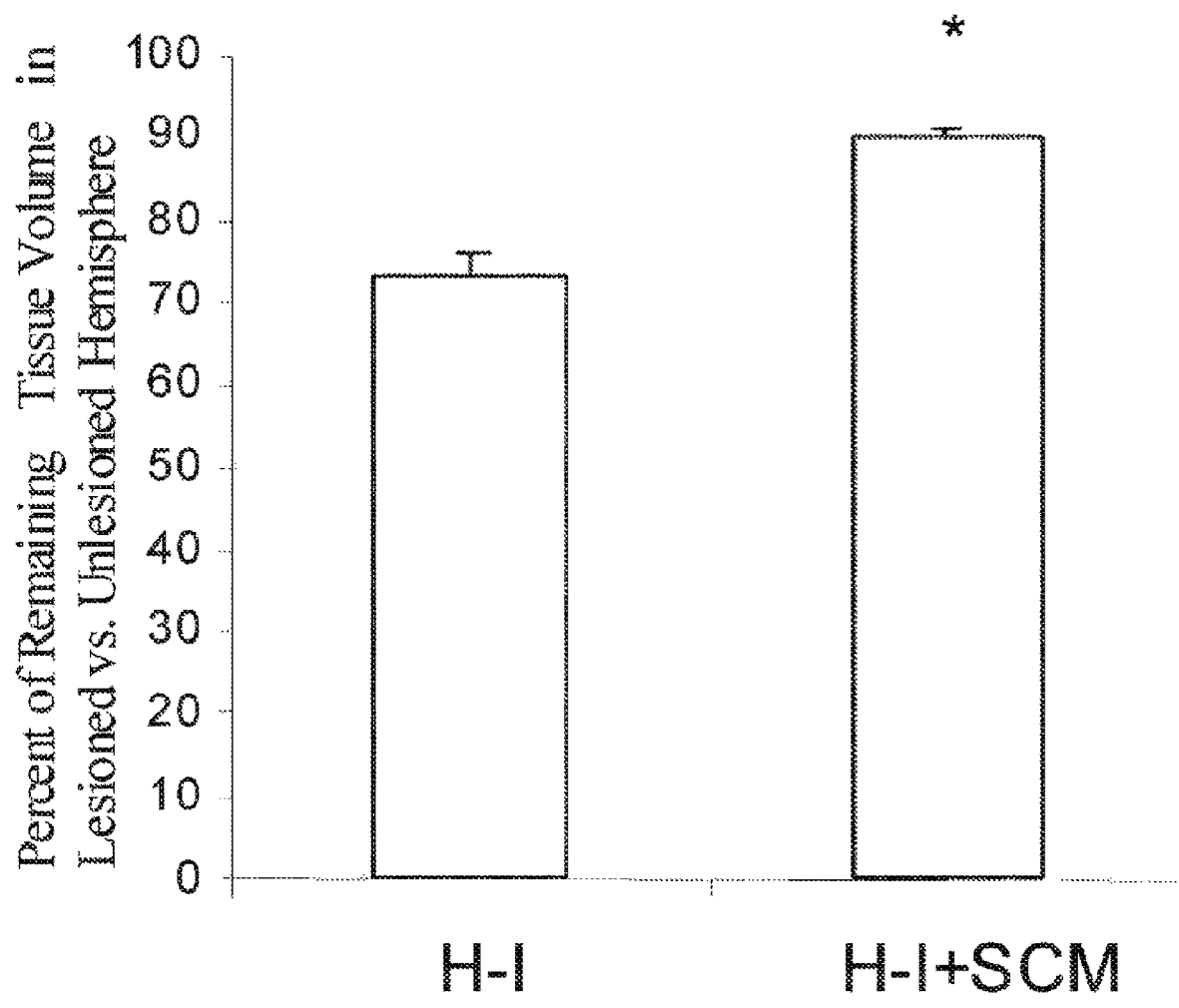
Figure 15:
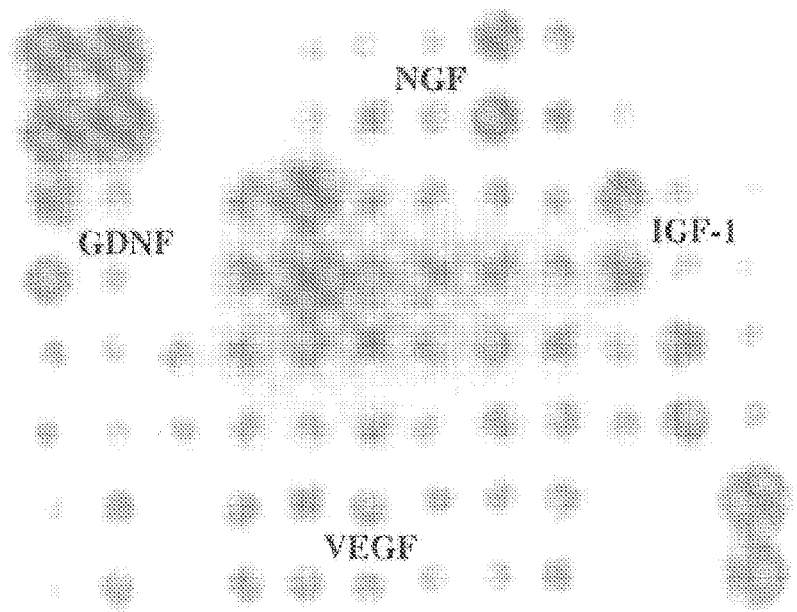
FIG. 15: Results of proteomic analysis of ASC Conditioned Media recovered from media contacted with ASCs in vitro. Specific proteins identified in this experiment include, but are not limited to, proteins related to neuroprotection: NGF (nerve growth factor), GDNF (glia-derived neurotrophic factor, IGF-1 (Insulin-like growth factor, and VEGF (vascular endothelia growth factor).

The oxygen and glucose deprivation (OGD) model highly correlates to mechanisms in action in the in vivo H-I model. The protective effect of ASC Conditioned Media was tested when added to primary mouse cortical neurons from 1-d old pups. The cultured neurons were placed in Hanks buffer without glucose and incubated for 2 hours in a hypoxic chamber (Forma Scientific) that was preset at 37° C. and 1% $O_2$. Neurons were then switched back to serum-free DMEM medium in the presence or absence of ASC Conditioned Media. 24 hours later, neurons were assayed by an LDH kit. As a control, neurons without OGD treatments were also switched into serum-free DMEM media in the presence or absence of ASC Conditioned Media to eliminate LDH effects from ASC Conditioned Media. Test results shown in FIG. 13 indicate that ASC Conditioned Media markedly protects neurons against OGD-induced neuronal injury.

E. 250× Enriched ASC Conditioned Media Protects Neurons Against H-I-Induced Hippocampal Neuronal Death In Vivo.

To investigate ASC Conditioned Media function in H-I-induced neuronal death in vivo, 7-d old Sprague Dawley rat pups were anesthetized with 2.5% halothane and the left carotid artery was permanently ligated. Hypoxic exposure was then achieved by placing pups in a 2.0-L airtight plastic chamber submerged in a 37.0° C. water bath and flushed for 2 h with a humidified mixture of 7% oxygen and 93% nitrogen. Pups were then returned to their dams until sacrifice. Pups (2 per group) received Intravenous (i.v.) injections of 10 μl of 250-fold concentrated rat ASC Conditioned Media 24 h after the hypoxic insult.

Figure 12:
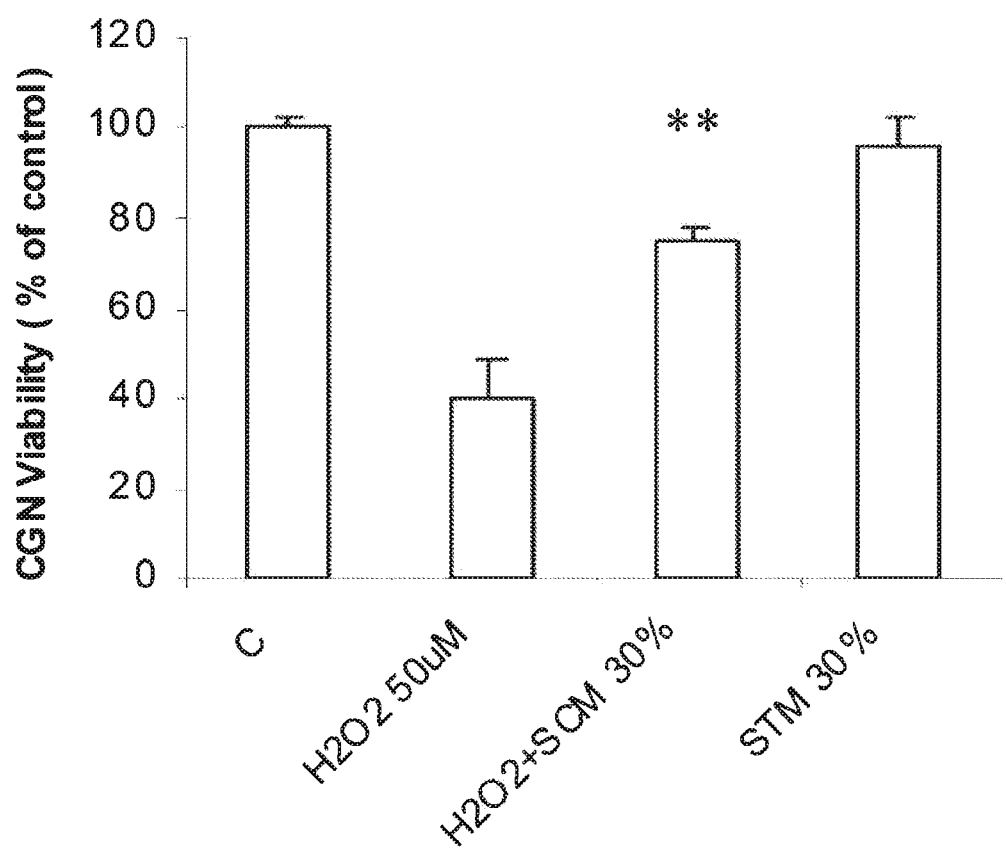
FIG. 12: ASC Conditioned Media protects CGN neurons against $H_2O_2$ (50 µM)-induced neuronal death. The ASC Conditioned Media was collected and subsequently added into the CGN cultures (at ⅓ of the final volume) that were then challenged by adding 50 µM of $H_2O_2$. Neuronal viability was quantified by staining neurons with MTT (Du, 2003). C, untreated CGN; H2O2 50 µM, CGN exposed to 50 µM $H_2O_2$ H2O2+SCM 30%, CGN exposed to 50 µM $H_2O_2$ and 30% ASC Conditioned Media; STM 30%, CGN exposed to 30% ASC Conditioned Media only.

The time period between H-I induction and ASC Conditioned Media injection was chosen because maximal disruption of the blood-brain barrier occurs at this time, allowing maximal penetration of large polypeptides into brain tissues (Ikeda, 1999; McLean 2004. Seven days following H-I injury, the brains were histologically analyzed to quantify the amount of damage to the hippocampus. In the hippocampus, H-I injury resulted in approximately 27% tissue loss when mice were exposed to hypoxia for 2 hours, as compared to non-injured controls. Conversely, FIG. 12 shows that mice treated with ASC Conditioned Media showed almost completely blocked brain damage.

As discussed above, ASC Conditioned Media effectively blocks neuronal death in models that involve different molecular mechanisms. These mechanisms include at least one of the following three pathways: JNK, p38, and caspase 3. These three pathways have been widely investigated and it is known that in addition to interacting each other, these pathways may also induce neuronal death independently (see Table I). Using these models, it is possible to determine if ASC-conditioned Media (ACASC Conditioned Media) inhibits injury stimuli-induced activation by phosphorylation of JNK and p38 and cleavage of caspase 3 in those models where they are actively involved (Table 1). According to our embodiment, a ASC Conditioned Media prepared as described protects neurons from neuronal death in these models via inhibition of ENK, JNK, p38, and/or caspase 3 activation.

The adipose tissue is minced (mouse and rat) then digested in Collagenase Type I solution (Worthington Biochemical, Lakewood, N.J.) under gentle agitation for 1 hour at 37° C., filtered with 500 μm and 250 μm Nitex filters, and centrifuged at 200 g for 5 minutes to separate the stromal cell fraction (pellet) from adipocytes. The ASC fraction is treated with red blood cell lysis buffer for 5 min at 37° C., then centrifuged at 300 g for 5 minutes. The supernatant is discarded and the cell pellet resuspended in the appropriate medium.

F. ASC Conditioned Media Protects Against OGD-Induced Cortical Neuronal Death.

Figure 18:
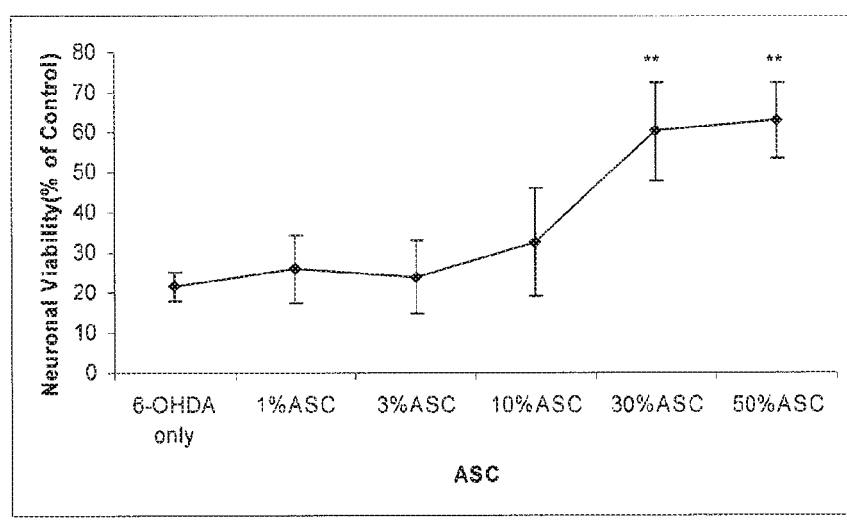
FIG. 18 displays the results of an experiment indicating that ASC-CM protects neurons against 6-hydroxydopamine (6-OHDA)-mediated death.

ASC-CM protects neurons against 6-hydroxydopamine (6-OHDA)-mediated death, as shown in FIG. 18. The ASC Conditioned Medium (ASC-CM) was collected and subsequently added to the cultured rat cerebellar granule neurons (CGN). Neuronal viability was quantified by either counting fluorescein positive neurons or staining living neurons with MTT. Since neurotoxicity induced by 6-OHDA was believed to be due, at least in part, to the production of reactive oxygen species (ROS). Also investigated were the levels of free radical generation in our model by using dihydroethidium (DHE) and dihydrorhodamine 123 (DHR). As shown in FIG. 18, exposure of CGN to 50 mM 6-OHDA resulted in significant increases in free radical production and CGN neuronal death.

G. ASC-CM Preserves the Cognitive Function of Rats Following Hypoxia-Ischemia Injury.

The ability of ASC-CM to provide long-term protection following hypoxia-Ischemia (HI) injury was determined as follows. HI injury was induced in 7 day old rat pups as described above. ASC-CM was administered at the time of surgery (pre-treatment) or 24 hours after HI injury (post treatment). Controls were uninjured rats (positive control) of the same age and rats receiving an equivalent volume of carrier (negative control). After 7 weeks the cognitive function of all rats was determined using the Morris Water Maze test.

Figure 17A:
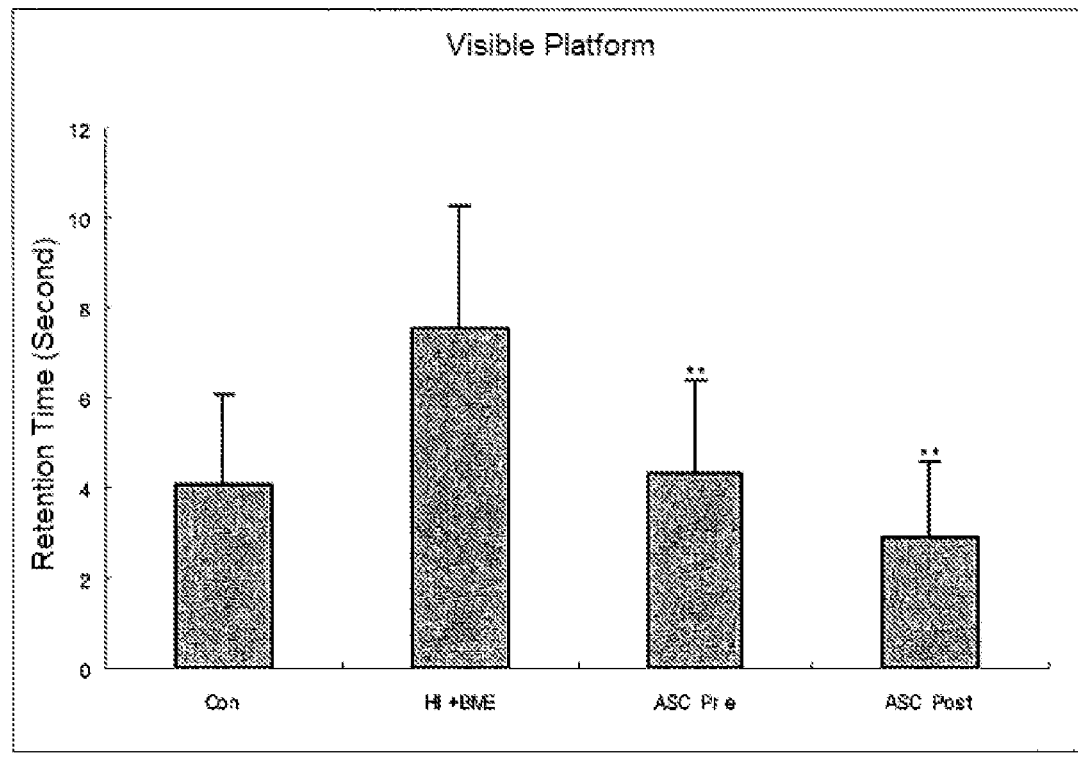
FIG. 17A and FIG. 17B: Results of tests showing that ASC-CM preserves the cognitive function of rats following hypoxia-ischemia injury, and utilizing the Morris Water Maze test.
Figure 17B:
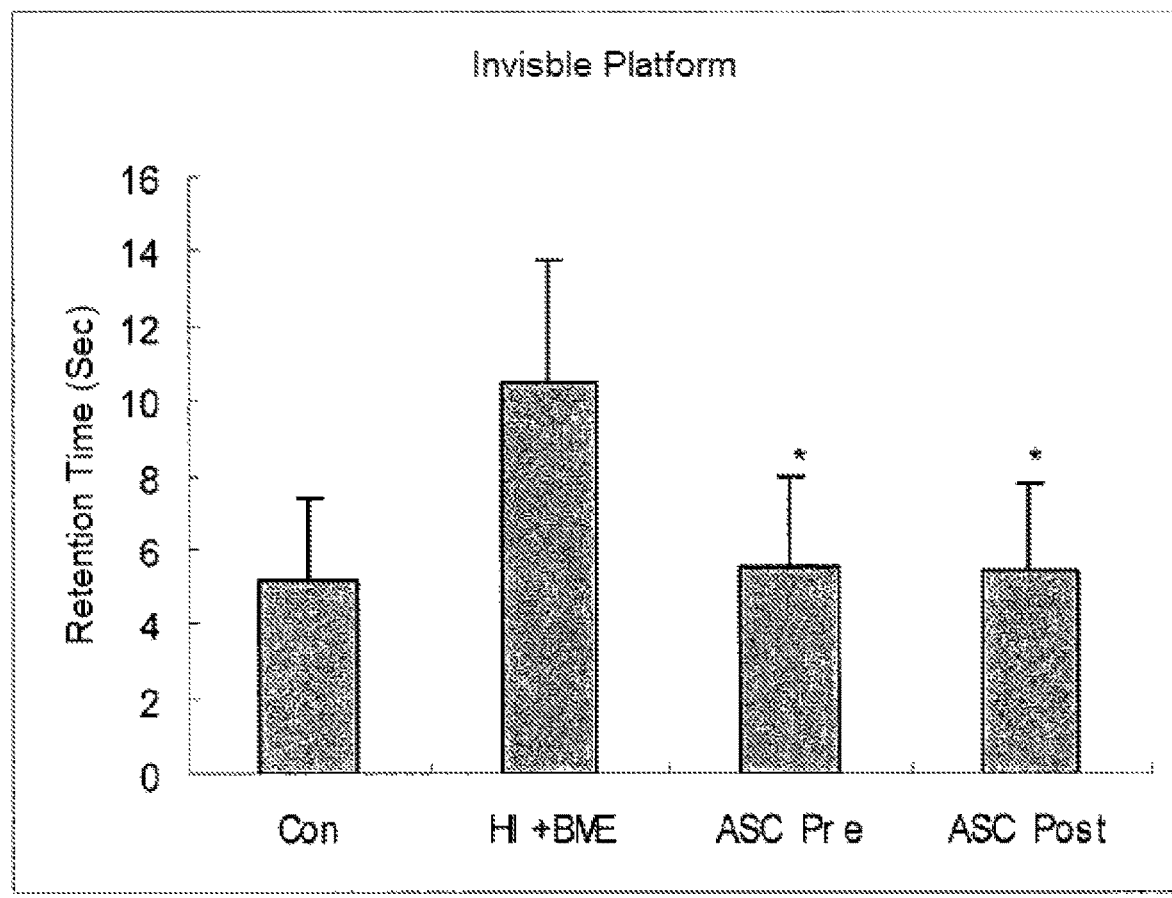

The test system consisted of a swimming pool containing a number of visual cues to facilitate orientation, including counters and decals. A 168 cm diameter, 41 cm high tank was filled to a depth of 30 cm with 15° C. water. A round transparent plastic platform, 11 cm in diameter, was placed in the pool so that the top of the platform was located 1 cm below the surface of the water, where it was not visible to a viewer on the surface of the water. For the visible platform test, a flag was placed on the platform. After performing the visible platform test, the flag was removed, making the platform not visible from the surface of the water (invisible test). Animals were individually placed at the same location in the water to begin the test. The time taken for the rats to reach the platform by swimming was recorded. Each animal was tested 3 times with 15 second intervals between repeats. Data are presented as mean±SEM. The results were compared using a paired Student's t-Test As shown on FIGS. 17A and 17B, for the visible platform test the time taken by the rats to first swim to the platform and then crawl out of the water onto the platform was much shorter for both ASC-pretreatment (n=3) and ASC-posttreatment (n=4) groups than for the control BME-treatment group (n=5) (**P<0.01). Similarly, ASC-CM treated rats performed better than BME control-treated rats in the invisible platform test (*P<0.05) (FIGS. 2A and 2B). These results demonstrate that ASC-CM treated rats have a higher level of cognitive function than control treated animals; thus, providing further evidence that ASC-CM provides protection against neurodegeneration.

IV. Methods

A. Preparation of Mouse and Rat CGN Neuronal Cultures and Analysis Method

CGN is prepared from 8-day-old rat or mouse pups as previously described (Du, 1997 and 2001). Preliminary data showed that mouse CGN behaves similarly to rat CGN. Briefly, freshly dissected cerebella is dissociated and the cells seeded at a density of 1.2 to 1.5×10$^6$ cells/ml on poly-L-lysine coated dishes in basal medium Eagle (Invirogen) supplemented with 10% FBS (Invirogen), 25 mM KCl, and gentamicin (0.1 mg/ml, Invitrogen). Cytosine arabinoside (10 µM, Sigma) is added to the culture medium 24 h after initial plating. All experiments utilize neurons after 7-8 days in vitro (DIV). The LK, glutamate, H2O2, MPP+, 6OHDA treatments follow methods that were previously described (Ni, 1997; Du, 1997a; Lin, 2003; Du, 1997b; Dodel, 1999). Viable neurons are quantified by counting fluorescein (green) positive cells which result from the de-esterification of fluorescein diacetate (FDA, Sigma) by living cells. Briefly, cultures are incubated with FDA (10 µg/ml) for 5 min, examined and photographed using UV light microscopy and the number of neurons from representative low power fields are counted as previously described (Du, 1997). Propidium iodide (PI, Sigma), which interacts with nuclear DNA producing a red fluorescence, is used to identify dead neurons. For PI staining, cultures are incubated with PI (5 µg/ml), examined and photographed using UV light microscopy as previously described (Du, 1997a).

B. Cultured Mesencephalic Neurons

Primary cultures of rostral mesencephalic tegmentum (RMT) dissected from E15 rat or E12 mouse embryos (Harlan) are performed using a modified method as previously described (Dodel, 1998). Preliminary studies show that mouse MDN behaves similarly to rat MDN. Briefly, RMT is dissociated using trypsin and DNase (Sigma) and the cells are be suspended in Dulbeccos Modified Eagle Medium (Invitrogen) supplemented with Ham F12 nutrient mixture (1:1; Invitrogen), glucose, 1% penicillin-streptomycin (Invitrogen) and 10% fetal bovine serum (Invitrogen). The cells are plated onto poly-L-lysine (10 µg/ml; Sigma) precoated 10 mm coverslips in 24-well plates at a density of 10$^5$ cells/cm$^2$ and incubated for 72 hr. Following 24 h the medium is supplemented with 10 µM cytosine arabinoside (Sigma) to inhibit glial cell proliferation. Neuronal cultures are used for experiments 7 days after preparation. Dopaminergic (DA) neurons in primary cultures are visualized by TH-immunohistochemistry using a primary monoclonal antibody against rat TH (Incstar) following by an anti-mouse IgG Cy3 conjugate (Sigma) (Dodel, 1998), and the number of TH-immunoreactive neurons is assessed using a Leitz inverted microscope (×200). Values are usually expressed as a % of control cultures for each experiment and the data are displayed as the mean±standard error of duplicate experiments, which are repeated about four times. The cell counts are statistically evaluated using analysis of variance.

Neurotoxicity is also examined by using methods of TUNEL (APOPTAG, ONCOR) and LDH (Roche) following manufacturers' instructions (Dodel, 1998).

C. Primary Neonatal Cortical Neuronal Culture

Cortices are collected from newborn rat or mice pups and minced. An aliquot of ice-cold PBS is added into the minced tissues, which are then centrifuged at 1000 rpm at 4° C. and the supernatants are discarded. An aliquot of 0.25% trypsin is added and incubated at 37° C. for 15 min to produce a single cell suspension (shaken once every 5 min). The precipitates are discarded and the supernatants are centrifuged again at 1000 rpm at 4° C. for 5 min. The cell pellets are diluted to an appropriate concentration with Neurobasal in 2% B27 (Invitrogen, Carlsbad, Calif., U.S.A.) and plated into poly-d-lysine-coated dishes (BD Biosciences, Franklin Lakes, N.J., U.S.A.). Usually, the cells are used between 4-6 days after plating. Before each treatment, cells are rinsed and then incubated in serum-free Dulbecco's modified Eagle's medium (DMEM) with or without high glucose (Invitrogen). All experiments are conducted under serum-free conditions. To induce OGD, neurons are placed in a hypoxic chamber (Forma Scientific) which is preset at 37° C. and 1% $O_2$. Neurons are incubated with serum-free DMEM media containing no glucose. Control neurons are incubated in the regular incubation chamber (37° C. and 21% $O_2$) in DEME containing high glucose. Four hours later, neurons are placed back to regular $CO_2$ incubator for another 20 h and then assayed using a LDH kit. For NMDA toxicity study, the neuronal culture is supplemented with 100 mM for 24 h and assayed using a LDH kit.

D. MTT Assay

Cell viability assays are performed in accordance with the protocol provided by R & D Systems (Minneapolis, Minn., U.S.A.). Briefly, cortical neurons from newborn rats are cultured in flat-bottomed, poly-d-lysine-coated, 96-well tissue culture plates (BioCoat, BD Biosciences). After each treatment, 100 µl of media is removed for the LDH assay and MTT is added to the cultures at 37° C. for 2.5 h. DMSO is then added to the cells. Cells are held for another 3 h at 37° C. in the dark since MTT is reduced by metabolically active cells into insoluble purple formazan dye crystals that are soluble in the DMSO. The absorption is read by a plate reader at 570 nm using a reference wavelength of 650 nm.

E. LDH Assay

About 100 µl of the culture media is monitored for the release of lactate dehydrogenase (LDH) to measure cell death, using a LDH kit from Roche, Indianapolis by following the manufacturer's instructions (Du, 1998). Each experiment is performed in triplicate; the data from a representative experiment carried out three times with similar results. The data is expressed as the mean OD±SD.

F. TUNEL Assay

DNA strand breaks are detected using terminal deoxynucleotidyl transferase-mediated biotinylated UTP nick end-labeling (TUNEL) according to the manufacturer's procedure (APOPTAG, ONCOR). Briefly, cultures are fixed for 30 min with 1% paraformaldehyde and then washed with PBS. 200 µl of Equilibration buffer is added to each well, followed by addition of 120 µl/well of working strength TdT cells are, then incubated for 30 min at 37° C. After adding 1 ml of working strength stop/wash buffer twice, 100 µl of working strength antibody solution (anti-digoxigenin-fluorescein) is added the mixture is held for 1 hr. The cells are visualized under phase-contrast microscopy. Apoptotic cells are discriminated morphologically by the presence of condensed, bright green nuclei in neurons.

G. Western Blot Analysis

Western blot analysis of ERK, JNK, p38, and active caspase is performed as previously described (Wei, 2004, Wei, 2005). Detection of caspase activity is also performed as described in 1997 (Du, 1997a,b). Neuronal extracts are prepared by lysing CGN at 1.5 and 3 h (for JNK and p38), 0, 3 and 6 h (ERK), and 20 h (for caspase 3) following insult treatments.

H. Proteomic Profiling of Neuroprotective Factors in Fractions from ASC-Conditioned Media Neuroprotective factors secreted by ASCs, are characterized using antibody arrays to identify specific factors present in fractions of conditioned medium. This information is used to assess the contribution of each factor to neuroprotective activity. An antibody array is used for initial characterization over other proteomics analyses because this method is sensitive (can detect pg level) and can directly measure the protein in media. In contrast, nucleic acid microarrays (SuperArray, Affymetrix, Agilent) can only detect mRNA changes and may not provide accurate data on protein production and secretion in to the media. Other methods for detecting proteins are much more powerful and can be used. Our data demonstrates that conditioned media from human ASCs potently protects rat neurons, suggesting that cross-species analyses and protection occurs.

I. Proteomic Profiling of Growth Factors/Cytokines Present in Conditioned Media

Active fractions from human and mouse ASC antibody can be identified using array membranes provided by RayBiotech. Detailed methodology is described in the company protocol; it is similar to Western blot protocols. In brief:

Step 1. Incubate the array membrane with 250-fold enriched ASCs supernatants.

Step 2. Incubate the factor-bound membrane with a cocktail of biotin-labeled antibodies.

Step 3. Incubate the array membrane with HRP-conjugated streptavidin.

Step 4. chemoluminescent detection.

The presence of any proteins detected by the array analyses can be confirmed in rat or murine (if not proved to be negative through probing the mouse array) conditioned media using antibodies or RT-PCR analyses, and the identified proteins can be manufactured using CDNA or other methods.

Because of the larger array of human antibodies, and conditions available it is more effective to probe for human proteins than it is to probe for specific proteins in rats, mice and other animals. However, mouse and rat ASCs may have unique properties that are not conserved across species. We do not believe that this is the case since our data demonstrate that human ASC conditioned media is a potent protector of rat neurons. However, the number of proteins detected by the arrays is still a fraction of the total number of proteins present in the media. It is possible that important factors in the conditioned media could go undetected. Accordingly, it may be necessary to use methods other than antibody detection to screen for factors in ACASC Conditioned Media produced by rat or mice cells. One such method is to use oligonucleotide array to identify components produced by ASCs. Commercially available oligonucleotide arrays include SuperArray, Affymetrix, or Agilent. The other arrays can be used to probe for factors that do not react with antibody assay. This technique provides information in the absence of antibodies and can be used directly with mouse and rat cells. If necessary, these two methodologies can be combined to overcome these inherit deficiencies of each separate method.

All references, patients, patient applications and the like cited herein and not otherwise specifically incorporated by references in their entirety, are hereby incorporated by references in their entirety as if each were separately incorporated by reference in their entirety.

An abstract is included to aid in searching the contents of the application it is not intended to be read as explaining, summarizing or otherwise characterizing or limiting the disclosure in any way.

The present disclosure contemplates modifications as would occur to those skilled in the art. It is also contemplated that processes embodied in the present disclosure can be altered, duplicated, combined, or added to other processes as would occur to those skilled in the art without departing from the spirit of the present disclosure.

Further, any theory of operation, proof, or finding stated herein is meant to further enhance understanding of the present disclosure and is not intended to make the scope of the present disclosure dependent upon such theory, proof, or finding.

While the disclosure has been illustrated and described in detail in the drawings and foregoing description, the same is considered to be illustrative and not restrictive in character, it is understood that only the preferred embodiments have been shown and described and that all changes and modifications that come within the spirit of the disclosure are desired to be protected.

The invention claimed is:

1. A stem cell conditioned medium, comprising:
   a cell culture supernatant containing at least one factor capable of exerting effective neuroprotection to treat a mammalian neural injury or insult, the cell culture supernatant produced by culturing at least one mesenchymal stem cell to produce the at least one factor, wherein the at least one mesenchymal stem cell comprises a marker profile of lin-/CD45-/c-kit-/CD90+/CD34+ marker before culturing and loses the CD34+ marker during culturing, wherein the at least one mesenchymal stem cell is a human mesenchymal stem cell.

2. The stem cell conditioned medium of claim 1, wherein the cell culture supernatant is produced by culturing the at least one mesenchymal stem cell in a first cell culture medium and later removing some or all of the first cell culture medium and further culturing the at least one mesenchymal stem cell in a second cell culture medium.

3. The stem cell conditioned medium of claim 2, wherein the second cell culture medium comprises a growth factor-free basal medium.

4. The stem cell conditioned medium of claim 2, wherein the first cell culture medium comprises a first amount of growth factor, wherein the second cell culture medium comprises a second amount of growth factor, and wherein the second amount is less than the first amount.

5. The stem cell conditioned medium of claim 2, wherein the cell culture supernatant is collected after the at least one mesenchymal stem cell has been cultured in the second cell culture medium.

6. The stem cell conditioned medium of claim 2, wherein the at least one mesenchymal stem cell is cultured in the second cell culture medium under a condition selected from the group consisting of a normoxic condition and a hypoxic condition.

7. The stem cell conditioned medium of claim 1, wherein the at least one factor is selected from the group consisting of at least one angiogenic factor and at least one antiapoptotic factor.

8. The stem cell conditioned medium of claim 1, wherein the at least one factor capable of exerting effective neuroprotection is capable of protecting against mammalian neuronal cell death.

9. The stem cell conditioned medium of claim 1, wherein the cell culture supernatant is concentrated to a concentration selected from the group of at least 50-fold, between 50-fold and 100-fold, at least 100-fold, between 100-fold and 250-fold, and at least 250-fold.

10. The stem cell conditioned medium of claim 1, wherein the cell culture supernatant is acted upon using a process selected from centrifugation, concentration, fractionation, lyophilization, and freeze-drying.

11. The stem cell conditioned medium of claim 1, wherein the supernatant comprises at least one chemical secretion from the cultured at least one mesenchymal stem cell, and wherein the at least one factor comprises a plurality of factors.

12. The stem cell conditioned medium of claim 1, wherein the at least one factor comprises at least two different factors having a synergistic effect on a target cell and/or organ.

13. A stem cell conditioned medium, comprising:
a supernatant containing at least one factor, the supernatant obtained by culturing at least one human mesenchymal stem cell in a first cell culture medium, switching the cell culture medium to a substantially growth factor-free second cell culture medium, and collecting the supernatant containing the at least one factor after switching the cell culture medium to the substantially growth factor-free second cell culture medium;
wherein the at least one human mesenchymal stem cell comprises a marker profile of lin-/CD45-/c-kit-/CD90+/CD34+ marker before culturing and loses the CD34+ marker during culturing.

14. The stem cell conditioned medium of claim 13, wherein the cell culture supernatant is fractionated to remove substances less than a specified kDa range selected from the group consisting of less than about 5 kDa, less than about 10 kDa, less than about 20 kDa, less than about 30 kDa, less than about 40 kDa, less than about 50 kDa, and greater than about 50 kDa.

* * * * *